United States Patent
Niki et al.

(10) Patent No.: US 9,314,415 B2
(45) Date of Patent: *Apr. 19, 2016

(54) SKIN LIGHTENING COMPOSITIONS

(71) Applicant: ELC Management LLC, New York, NY (US)

(72) Inventors: Yoko Niki, Kakogawa (JP); Masaki Yoshida, Kuwana (JP); Masamitsu Ichihashi, Kobe (JP); Hideya Ando, Takatsuki (JP); Daniel B. Yarosh, Merrick, NY (US); Mary S. Matsui, Teaneck, NJ (US)

(73) Assignee: ELC MANAGEMENT LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/037,571

(22) Filed: Sep. 26, 2013

(65) Prior Publication Data

US 2015/0086497 A1    Mar. 26, 2015

Related U.S. Application Data

(62) Division of application No. 12/984,159, filed on Jan. 4, 2011, now Pat. No. 8,722,026.

(60) Provisional application No. 61/292,577, filed on Jan. 6, 2010.

(51) Int. Cl.
| | |
|---|---|
| A61Q 19/02 | (2006.01) |
| A61Q 17/04 | (2006.01) |
| A61K 8/49 | (2006.01) |

(52) U.S. Cl.
CPC ............ *A61K 8/4946* (2013.01); *A61K 8/49* (2013.01); *A61Q 17/04* (2013.01); *A61Q 19/02* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 3,215,724 A | 11/1965 | Strobel et al. | |
| 3,439,088 A | 4/1969 | Edman | |
| 3,781,417 A | 12/1973 | Welters et al. | |
| 3,818,105 A | 6/1974 | Coopersmith et al. | |
| 4,359,465 A | 11/1982 | Ruwart | |
| 4,677,152 A | 6/1987 | Allen et al. | |
| 4,689,331 A | 8/1987 | Ankner et al. | |
| 4,702,844 A | 10/1987 | Flesher et al. | |
| 4,746,667 A | 5/1988 | Carisson et al. | |
| 4,803,067 A | 2/1989 | Brunetta et al. | |
| 4,970,252 A | 11/1990 | Sakuta et al. | |
| 5,077,211 A | 12/1991 | Yarosh | |
| 5,093,342 A | 3/1992 | Tomoi et al. | |
| 5,118,496 A | 6/1992 | Herstein | |
| 5,183,588 A | 2/1993 | Salerno et al. | |
| 5,183,589 A | 2/1993 | Brunetta et al. | |
| 5,190,762 A | 3/1993 | Yarosh | |
| 5,236,986 A | 8/1993 | Sakuta | |
| 5,272,079 A | 12/1993 | Yarosh | |
| 5,296,231 A | 3/1994 | Yarosh | |
| 5,411,741 A | 5/1995 | Zalas | |
| 5,412,004 A | 5/1995 | Tachibana et al. | |
| 5,654,362 A | 8/1997 | Schulz, Jr. et al. | |
| 5,714,505 A | 2/1998 | Hasselkus | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,843,193 A | 12/1998 | Hawkins et al. | |

(Continued)

FOREIGN PATENT DOCUMENTS

| | | |
|---|---|---|
| EP | 0068378 | 1/1983 |
| EP | 1657242 | 5/2006 |

(Continued)

OTHER PUBLICATIONS

Eberlein-Konig, MD, et al.; Protective effect against sunburn of combined systemic ascorbic acid (vitamin C) and d-a-tocopherol (vitamin E); Journal of the American Academy of Dermatology; pp. 45-48; Jan. 1998.

(Continued)

*Primary Examiner* — Jyothsna Venkat
(74) *Attorney, Agent, or Firm* — Cynthia R. Miller

(57) ABSTRACT

Compositions and methods for lightening and/or depigmenting skin are provided, the compositions comprising compounds having the structure:

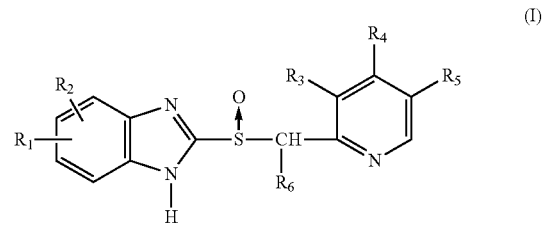

or having the structure:

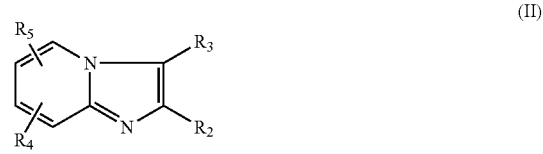

as defined herein.

3 Claims, 1 Drawing Sheet

(56) References Cited

U.S. PATENT DOCUMENTS

| | | | |
|---|---|---|---|
| 6,245,795 | B1 | 6/2001 | Takahashi et al. |
| 6,497,860 | B1* | 12/2002 | Kawato et al. ................. 424/62 |
| 6,509,010 | B2 | 1/2003 | Beck et al. |
| 8,722,026 | B2 | 5/2014 | Niki et al. |
| 8,992,897 | B2 | 3/2015 | Niki et al. |
| 2002/0146376 | A1 | 10/2002 | Beck et al. |
| 2004/0180919 | A1 | 9/2004 | Miller et al. |
| 2005/0020620 | A1 | 1/2005 | Weigl et al. |
| 2005/0196418 | A1 | 9/2005 | Yu et al. |
| 2006/0034875 | A1 | 2/2006 | Nakanishi et al. |
| 2007/0042997 | A1 | 2/2007 | Itai et al. |
| 2007/0093551 | A1 | 4/2007 | Yu et al. |
| 2007/0104783 | A1 | 5/2007 | Domb et al. |
| 2008/0113037 | A1 | 5/2008 | Green et al. |
| 2008/0124381 | A1 | 5/2008 | Barnhart et al. |
| 2008/0160106 | A1 | 7/2008 | Fais et al. |
| 2008/0287502 | A1 | 11/2008 | Hsu et al. |
| 2009/0227633 | A1 | 9/2009 | Damaj |
| 2011/0171149 | A1 | 7/2011 | Niki et al. |
| 2012/0142738 | A1 | 6/2012 | Stephan et al. |
| 2013/0231372 | A1 | 9/2013 | Matsui et al. |

FOREIGN PATENT DOCUMENTS

| | | |
|---|---|---|
| JP | H05124925 | 5/1993 |
| JP | 6118708 | 4/1994 |
| JP | 2002-515885 | 5/2002 |
| WO | WO-98/15276 | 4/1998 |
| WO | WO 99/56720 | * 11/1999 |
| WO | WO-99/63940 | 12/1999 |
| WO | WO-2004024798 | 3/2004 |
| WO | WO-2004/080430 | 9/2004 |
| WO | WO-2007070983 | 6/2007 |
| WO | WO-2010/119102 | 10/2010 |

OTHER PUBLICATIONS

Altman, Kenneth W., et al.; Proton Pump (H+/K+ -ATPase) Expression in Human Laryngeal Seromucinous Glands; Otolaryngology-Head and Neck Surgery (2005); vol. 133; pp. 718-724.
Ancans, Janis, et al.; Melanosomal pH Controls Rate of Melanogenesis, Eumelanin/Phaeomelanin Ratio and Melanosome Maturation in Melanocytes and Melanoma Cells; Experimental Cell Research 268(1); pp. 26-35; Aug. 2001; Academic Press, Orlando, FL.
Ancans, Janis, et al.; Melansomal pH, Pink Locus Protein and their Roles in Melanogenesis; The Journal of Investigative Derm; vol. 117; pp. 158-159; Jul. 2001.
Aroca, Pilar, et al.; Specificity of dopachrome tautomerase and inhibition by carboxylated indoles; Biochem. J.; vol. 277; pp. 393-397; 1991.
Asano S., et al.; Mutational Analysis of Putative SCH28080 Binding Sites of the Gastric H+, K+ -ATPase; Journal of Biological Chemistry; vol. 272, No. 28; pp. 17668-17674; 1997.
Axelsen, Kristian B., et al.; Evolution of Substrate Specifications in the P-Type ATPase Superfamily; Journal of Molecular Evolution 1998; vol. 46; pp. 84-101.
Basrur, Venkatesha, et al.; Proteomic Analysis of Early Melanosomes: Identification of Novel Melanosomal Proteins; Journal of Proteome Research; vol. 2 No. 1; pp. 69-79; 2003.
Beil, W., et al.; Mechanism of gastric antisecretory effect of SCH 28080; Br. J. Pharmac 88; pp. 19-23; 1986.
Berkowitz, Barry A., PhD, et al.; Life Cycle of a Block Buster Drug; Discovery and Development of Omeprazole (Prilosec™); Speaking of Pharmacology; Molecular Interventions; vol. 2 Issue 1; pp. 6-11 ; Feb. 2002.
Besancon, Marie, et al.; Membrane Topology and Omeprozole Labeling of the Gastric H+, K+ -Adenosinetriphosphatase; Biochem1993; vol. 32 No. 9; pp. 2345-2355.
Besancon, Marie, et al.; Sites of Reaction of the Gastric H, K-ATPase with Extracytoplasmic Thiol Reagents; The Journal of Biological Chem; vol. 272 No. 36, Issue of Sep. 5; pp. 22438-22446; 1997.

Bhatnagar, V., et al.; pH of Melanosomes of B16 Murine Melanoma is Acidic; Its Physiological Importance in the Regulation of Melanin Biosynthesis; Arch. Biochem. Biophys.; vol. 307; pp. 183-192; 1993.
Brilliant, Murray H.; The Mouse p (pink-eyed dilution) and Human P Genes, Oculocutaneous Albinism Type 2 (OCA2) and Melanosomal pH; Pigment Cell Res 14; pp. 86-93; 2001.
Brilliant, Murray, et al.; Melanosomal pH, Pink Locus Protein and their Roles in Melanogenesis; The Journal of Investigative Dermatology; vol. 117 No. 2; pp. 386-387; Aug. 2001.
Chang, H., et al.; Proton Transport by Gastric Membrane Vesicles; Biochim et Biophysica Acta; vol. 464(2); pp. 313-327; 1977.
Cheli, Yann, et al.; Alpha-MSH and cyclic-AMP elevating agents control Melanosome pH through a PKA-independent mechanism; The Journal of Biological Chem; vol. 284 No. 28; pp. 18699-18706; Jul. 2009.
Cheli, Yann, et al.; Alpha-MSH and cyclic-AMP elevating agents control melanosome pH through a PKA-independent mechanism; The Journal of Biological Chemistry; pp. 1-11, Figs. 1-7; Published on Apr. 22, 2009 as Manuscript M109.005819; Downloaded from www.jbc.org on Jun. 23, 2009.
Chow, Dar C., et al.; Functional Significance of the β-Subunit for Heterodimeric P-Type ATPases; The Journal of Experimental Bio 198; pp. 1-17; 1995.
Devi, C.C., et al.; pH-dependent Interconvertible Allosteric Forms of Murine Melanoma Tyrosinase: Physiological Implications; Eur. J. Biochem. 166; pp. 705-711; 1987.
Fitzparick, T.B., Ultravioletinduced Pigmentary Changes: benefits and hazards; Curr. Probl. Dermatol.; vol. 15; pp. 25-38; 1986; Karger. Basel, New York.
Fuller, Bryan B., et al.; Regulation of the Catalytic Activity of Pre-existing Tyrosinase in Black and Caucasian Human Melanocyte Cell Cultures; Experimental Cell Research 262(2); pp. 197-208; Jan. 2001; Academ Press, Orlando, FL.
Ginger, Rebecca S.; SLC24A5 Encodes a trans-Golgi Network Protein with Potassium-dependent Sodium-Calcium Exchange Activity that Regulates Human Epidermal Melanogenesis; The Journal of Biological Chem; vol. 283 No. 9; pp. 5486-5495; Feb. 2008.
Grabe, M., et al.; Regulation of Organelle Acidity; J. General Physiol.; vol. 117; pp. 329-344; 2001.
Gunathiliake, R.; et al.; pH-regulated Mechanism Accounts for Pigment-Type Differences in Epidermal Barrier Function; Journal of Investigative Derm; vol. 129; pp. 1719-1729; 2009.
Halaban, Ruth, et al.; Abnormal Acidification of Melanoma Cells Induces Tyrosinase Retention in the early Secretory Pathway; The Journal of Biological Chem; vol. 277 No. 17, Issue Apr. 26; pp. 14821-14828; 2002.
Hearing, V.J.; The Regulation of Melanin Formation; The Pigmentary System: Physiology and Pathophysiology, 2nd Edition; pp. 191-212; 2006; Blackwell Publishing Ltd., Malden, MA USA.
Hearing. V.J., et al.; A Comparison of Tyrosine Hydroxylation and Melanin Formation; J. Biochem. 157; pp. 549-557; 1976.
Herzing, Laura B.K., et al.; The Human Aminophospholipid-Transporting ATPase Gene ATP10C Maps Adjacent to UBE3A and Exhibits Similar Imprinted Expression; Am. J. Human Genetics 68; pp. 1501-1505; 2001.
Kimura, Tohru, et al.; Mutational Study on the Roles of Disulfide Bonds in the β-Subunit of Gastric H+, K+ -ATPase; The Journal of Biological Chem; vol. 277 No. 23, Issue of Jun. 7; pp. 20671-20677; 2002.
Kirchheiner, Julia, et al.; Relative potency of proton-pump inhibitors-comparison of effects on intragastric pH; Eur J. Clin Pharmacol 65; pp. 19-31; 2009.
Mani, Indu, et al.; Interaction of Melanin with Proteins—The Importance of an Acidic Intramelanosomal pH; Pigment Cell Res 14; pp. 170-179; 2001.
Mattsson Jan P.; Omeprazole and bafilomycin, two proton pump inhibitors: differential of their effects on gastric, kidney and bone H+ -translocating ATPase; Biochimica et Biophysics Acta; vol. 1065; pp. 261-268; Jun. 1991.
Moellmann, G., et al.; Regulation of Melanogenesis in Melanocytes; Pigment Cell Res., Supp. 1; pp. 79-87, 1988.
NDA 19-810/s-067 and S-080; Prilosec (Omeprazole) Delayed-Release Capsules; pp. 3-25; 9194138 640004-38; 2003; AstraZeneca.

(56) References Cited

OTHER PUBLICATIONS

Nelson, Nathan, et al.; The Cellular Biology of Proton-Motive Force Generation by V-ATPases; The Journal of Experimental Bio 203; pp. 89-95; 2000.
Olbe, Lars, et al.; A Proton-Pump Inhibitor Expedition: The Case Histories of Omeprazole and Esomeprazole; Nature Reviews Drug Discovery; vol. 2; pp. 132-139; Feb. 2003.
PCT International Search Report; International Application No. PCT/US2011/020240; Completion Date: Sep. 20, 2011; Mailing Date: Sep. 20, 2011.
PCT International Search Report; International Applicaton No. PCT/US2013/027670; Completion Date: Jun. 25, 2013; Mailing Date: Jun. 26, 2013. (11.45).
PCT Written Opinion of the International Searching Authority; International Applicaton No. PCT/US2013/027670; Completion Date: Jun. 25, 2013; Mailing Date: Jun. 26, 2013. (11.45).
PCT Written Opinion; International Application No. PCT/US2011/020240; Completion Date: Sep. 20, 2011; Mailing Date: Sep. 20, 2011.
Pearce, C.M., et al.; Microbiological production of omeprazole metabolites by Cunninghamella elegans; Journal of Molecular Catalysis B: Enzymatic, 2006; vol. 41; pp. 87-91; See fig. I.
Petris, Michael, J., et al.; The Menkes copper transporter is required for the activation of tyrosinase; Human Molecular Genetics; vol. 9 No. 19; pp. 2845-2851; 2000.
Puri, Nelu, et al.; Aberrant pH of Melansomes in Pink-Eyed Dilution (p) Mutant Melanocytes; The Journal of Investigative Derm: The p Protein and Melanosomal pH; vol. 115 No. 4; pp. 607-613; Oct. 2000.
Qaisi, A. M., et al.; Acid Decomposition of Omeprazole in the Absence of Thiol: a Differential Pulse Polarographic Study at the Static Mercury Drop Electrode (SMDE); Journal of Pharm Sciences; vol. 95(2); pp. 384-391; 2006 (Abstract only).
Ramaiah, A.; Lag Kinetics of Tyrosinase: Its Physiologic Implications; Indian J. Biochem. And Biophys; vol. 33; pp. 349-356; 1996.
Reinhardt, Jurgen, et al.; Differential localization of human nongastric H+ -K+ -ATPase ATP1AL1 in polarized renal epithelial cells; Am J Renal Physiol 279; pp. F417-F425; 2000.
Ritter, M., et al.; Effect of inhibitors of Na+/H+ -exchange and gastric H+/K+ ATPase on cell volume, intracellular pH and migration of human polymorphonuclear leucocytes; British Journal of Pharm 124; pp. 627-638; 1998.
Robinson, M., et al.; Clinical Pharmacology of Proton Pump Inhibitors: What the Practicing Physician Needs to Know; Drugs, 63; pp. 2739-2754; 2003.
Roche, Victoria F., PhD; The Chemically Elegant Proton Pump Inhibitors; American Journal of Pharmaceutical Education; 70(5) Article 101; pp. 1-11; 2006.
Sachs G., et al.; The Gastric H+K+ -ATPase: The Site of Action of Omeprazole; Scandinavian Journal of Gastroenterology, 24; vol. 166; pp. 3-11, 1989.
Sachs, G., et al.; Review article: the clinical pharmacology of proton pump inhibitors; Alimentary Pharmacology & Therapeutics; Suppl. 2; pp. 2-8; 2006; Blackwell Pub Ltd.
Saeki, H., et al.; Stimulation of Ionophores of Tyrosinase Activity of Mouse Melanoma Cells in Culture; Journal of Investigative Dermatology; vol. 85, No. 5; pp. 423-425; 1985.
Setty, Subba Rao Gangi, et al.; Cell-specific of ATP7A transport sustains copper-dependent tyrosinase activity in melanosomes; Nature; vol. 454, 28; pp. 1142-1147; Aug. 2008.
Slominski, Andrzej., et al.; Melanin Pigmentation in Mammalian Skin and Its Hormonal Regulation; Physiological Reviews; vol. 84; pp. 1155-1228; Oct. 2004.
Smith, Dustin R., et al.; The relationship between Na+/H+ exchange expression and tyrosinase activity in human melanocytes; Experimental Cell Res 298; pp. 521-534; 2004.
Sturm, Richard A.; et al.; Human pigmentation genes: Identification, structure and consequences of polymorphic variation; Gene: an International Journal on Genes and Genomes; pp. 49-62; 2001.
Tabata, Hiroyuki, et al.; Vacuolar-type H+ -ATPase with the a3 isoform is the proton pump on premature melanosomes; Cell and Tissue Research; vol. 332 Issue 3; p. 447-460; 2008.
Tabuchi, Yoshiaki, et al., Cibenzoline, an ATP-sensitive K+ channel blocker, binds to the K+ -binding site from the cytoplasmic side of gastric H+, K+, -ATPase; British Journal of Pharm; vol. 134(8); pp. 1655-1662; 2001.
Townsend, D., et al.; Optimized Assay for Mammalian Tyrosinase (Polyphenol Phenyloxidase); Analytical Biochemistry, 139; pp. 345-352; 1984; Academic Press, Orlando, FL.
Vagin, Olga, et al.; Polarized membrane distribution of potassium-dependent on pumps in epithelial cells; Different roles of the N-glycans of their β subunits; Cell Biochem Biophys 47; pp. 376-391; 2007.
Patil, Avinash, et al.; A Systematic Review of Benzimidazole Derivatives as an Antiulcer Agent; Review of Benzimidazole Derivatives; Rasayan J. Chem; 2008; pp. 447-460; vol. 1, No. 3; e-mail: avinashay_princ@rediffmail.com.
Reddy; A study on process impurity profile of rabeprazole, omeprazole and synthesis of their derivatives; pp. 101-139; http://shodhganga.inflibnet.ac.in/bitstream/10603/2187/13/13_chapter%204.pdf. PhD Thesis of Pingili Ramchandra Reddy.
Ahmed, Z., et al.; Cisplatin sensitivity of oral squamous carcinoma cells is regulated by Na, K, -ATPase activity rather than copper-transporting P-type ATPases, ATP7A and ATP7B; Cancer Chemother Pharmacol (2009) 63; pp. 643-650.
Almirante, et al.; Derivatives of Imidazole. III. Synthesis and Pharmacological Activities of Nitriles, Amides, and Carboxylic Acid Derivatives of Imidazo [1,2-a] pyridine; Journal of Medicinal Chemistry; 1969; pp. 122-126.
Barnes, N., et al.; The copper-transporting ATPases, Menkes and Wilson disease proteins, have distinct roles in adult and developing cerebellum. J Biol Chem. 2005; 280:96940-9645.
Bartee, M.Y., et al.; Hepatic copper-transporting ATPase ATP7B: function and inactivation at the molecular and cellular level. Biometals 2007; 20:627-637.
Boal, A.K, et al.; Crystal structures of cisplatin bound to a human copper chaperone. J Am chem. Soc. 2009; 131(40):14196-14197.
D'Amico, F., et al.; Menkes protein localization in rat parotid acinar cells. Acta Histochem. 2005; 107: 373-378.
DeMilito, A. and Fais, S.; Proton pump inhibitors may reduce tumour resistance; Expert Opin. Pharmacother. (2005); 6(7); pp. 1049-1054; 2005 Ashley Pub.
DiDonato, M., et al.; Expression, purification, and metalbinding properties of the N-terminal domain from the Wilson disease putative copper-transporting ATPase (ATP7B). J Biol Chem. 1997; 272(52):33279-33282.
Dierick, H., et al.; Immunocytochemical localization of the Menkes copper transport protein (ATP7A) to the trans-Golgi network; Human Molecular Genetics 1997; vol. 6 No. 3: pp. 409-416; 1997 Oxford University.
Dmitriev, O., et al.; Mechanism of tumor resistance to cisplatin mediated by the copper transporter ATP7B; Biochem Cell Biol. 89 pp. 138-147; 2011; NRC Research Press.
Dmitriev, O., et al.; Solution structure of the N-domain of Wilson disease protein: distinct nucleotide-binding environment and effects of disease mutation. Proc Natl Acad Sci U.S.A. 2006; 103(14):5302-5307.
Francis, M. J., et al.; Identification of a di-leucine motif within the C terminus domain of the Menkes disease protein that mediates endocytosis from the plasma membrane. J Cell Sci. 1999; 112(Pt 11):1721-1732.
Gourdon, P., et al.; Crystal structure of a copper-transporting PIB-type ATPase; Nature vol. 475; pp. 59-64; Jul. 2011.
Greenough, M., et al.; Signals regulating trafficking of Menkes (MNK; ATP7A) copper-translocating P-type ATPase in polarized MDCK cells. Am J Physiol Cell Physiol. 2004; 287:C1463-C1471.
Guo, Y., et al.; NH2-terminal signals in ATP7B Cu-ATPase mediate its Cu-dependent anterograde traffic in polarized hepatic cells. Am J Physiol Gastrointest Liver Physiol. 2005; 289:G904-G916.
Hamza, I., et al.; The metallochaperone Atox 1 plays a critical role in perinatal copper homeostasis. Proc Natl Acad Sci USA. 2001; 98:6848-6852.

(56) References Cited

OTHER PUBLICATIONS

Harris, E.D.; Cellular copper transport and metabolish; 2000; Annu Rev Nutr. 20; 291-310.

Hung, Y. H., et al.; Purification and membrane reconstitution of catalytically active Menkes copper-transporting P-type ATPase (MNK; ATP7A). Biochem. J. 2007; 401:569-579.

Kalayda, G., et al.; Altered localisation of the copper efflux transporters ATP7A and ATP7B associated with cisplatin resistance in human ovarian carcinoma cells; BMC Cancer 8, 175; pp. 1-12; Jun. 2008.

Kodama, H., et al.; Clinical manifestations and treatment of Menkes disease and its variants. Pediatr Int. 1999; 41:423-429.

Komatsu, M., et al.; Copper-transporting P-type adenosine triphosphatase (ATP7B) is associated with cisplatin resistance. Cancer Res. 2000; 60(5):1312-1316.

Lane, C., et al.; Studies on endocytic mechanism of the Menkes copper-translocating P-type ATPase (ATP7A, MNK). Endocytosis of the Menkes protein. Biometals. 2004; 17:87-98.

Leonhardt, K., et al.; Functional Interactions of Cu-ATPase ATP7B with Cisplatin and the Role ATP7B in the Resistance of Cells to the Drug. J. Biol. Chem.; Mar. 20, 2009; 284(12): 7793-7802.

Luciani, F., et al.; Effect of Proton Pump Inhibitor Pretreatment on Resistance of Solid Tumors to Cytotoxic Drugs; Journal of the National Cancer Institute; vol. 96 No. 22; pp. 1702-1713; Nov. 2004.

Lutsenko, S., et al.; Biochemical basis of regulation of human copper-transporting ATPases. Arch Biochem Biophys. 2007b; 463(2): 134-148.

Lutsenko, S., et al.; Cellular multitasking: The dual role of human Cu-ATPases in cofactor delivery and intracellular copper balance. Arch Biochem Biophys. 2008; 476(1): 22-32.

Lutsenko, S., et al.; N-terminal domains of human copper-transporting adenosine triphosphatases (the Wilson's an Menkes disease proteins) bind copper selectively in vivo and in vitro with stoichiometry of one copper per metal-binding repeat. J. Bio Chem. 1997; 272(30): 18939-18944.

Mandal, A. K., et al.; Functional roles of metal binding domains of the Archaeoglobus flugidus Cu(+)-ATPase CopA. Biochemistry. 2003; 42:11040-11047.

Menkes, J., et al.; A Sex-Linked Recessive Disorder with Retardation of Growth, Peculiar Hiar, and Focal Cerebral and Cerebellar Degeneration; Pediatrics, May 1962; pp. 764-779.

Mercer, J. F., et al.; Copper-induced trafficking of the Cu-ATPases: a key mechanism for copper homeostasis. Biometals. 2003; 16:175-184.

Nakagawa, T.; et al.; Expression of copper-transporting P-type adenosine triphosphatase (ATP7B) correlates with cisplatin resistance in human non-small cell lung cancer xenografts. Oncol. Rep. 2008; 20(2):265-270.

Petris, M., et al.; The Menkes protein (ATP7A; MNK) cycles via the plasma membrane both in basal and elevated extracellular copperusing a C-terminal di-leucine endocytic signal; Human Molecular Genetics 1999; vol. 8 No. 11; pp. 2107-2115; 1999 Oxford University.

Ralle, M., et al.; Copper transfer to the N-terminal domain of the Wilson disease protein (ATP7B): X-ray absorption spectroscopy of reconstituted and chaperone-loaded metal bind domains and their interaction with exogenous ligands. J Inorg Bioch. 2004:98:765-774.

Robinson, N.; A platform for copper pumps; Nature vol. 475; pp. 41-42; Jul. 2011.

Wilson, S. K.; Progressive lenticular degeneration: a familial nervous disease associated with cirrhosis of the liver. Brain. 1912; 34: pp. 295-366.

Wilson, S. K.; Progressive lenticular degeneration: a familial nervous disease associated with cirrhosis of the liver. Brain. 1912; 34: pp. 367-439.

Wilson, S. K.; Progressive lenticular degeneration: a familial nervous disease associated with cirrhosis of the liver. Brain. 1912; 34:pp. 440-509.

Abelo, et al.; Pharmacodynamic Modelling of Irreversible and Reversible Gastric Proton Pump Inhibitors; Comprehensive Summaries of Uppsala Dissertations from the Faculty of Pharmacy 303; ACTA Universitatis Upsaliensis; Dec. 2003; (54 pages).

Dent, et al.; A randomized, comparative trial of a potassium-competitive acid blocker (AZD0865) and esomeprazole for the treatment of patients with nonerosive reflux disease; The American Journal of Gastroenterology; 103, pp. 20-26; Jan. 2008. (Abstract Only).

Ito, et al.; Pharmacological Profile of Novel Acid Pump Antagonist 7-(4-fluorobenzyloxy)-2,3-dimethyl-1-{[(1S,2S)-2-methyl cyclopropyl]methyl}-1H-pyrrolo[2,3-d]pyridazine (CS-526); The Journal of Pharmacology and Experimental Therapeutics; vol. 323; No. 1; pp. 308-317; http://www.ncbi.nlm.nih.gov/pubmed/17630360; Jul. 2007.

Lynch, Dr.; MTHFR Mutations and Antacids are a Bad Mix; MTHFR Mutations and Antacids are a Bad Mix—MTHFR.Net; http://mthfr.net/mthfr-mutations-and-antacids-are-a-bad-mix/2011/09/22/; Sep. 2011.

Scott, et al.; Inhibition of H+K+ATPase by SCH 28080 and SCH 32651; European Journal of Pharmacology; Sigma-Aldrich; vol. 112, Issue 2; pp. 268-270; Jun. 1985. (Abstract Only).

Simon, et al.; Soraprazan: Setting New Standards in Inhibition of Gastric Acid Secretion;The Journal of Pharmacology and Experimetnal Therapeutics; vol. 321; No. 3; pp. 866-874; Mar. 2007.

Swathi, et al.; Proton Pump Inhibitors; HYGEIA; vol. 1; No. 1; pp. 28-32; Mar.-Aug. 2009.

Brenner, et al.; Modifying skin pigmentation—approaches through intrinsic biochemistry and exogenous agents; Drug Discovery Today: Disease Mechanisms; vol. 5; No. 2; pp. e189-e199; 2008.

Namazi, et al.; Can Proton Pump Inhibitors Accentuate Skin Aging?; Archives of Medical Research 41; pp. 147-148; 2010.

Namazi, M.R.; Proton pump inhibitors may trigger vitiligo by rendering melanocytes prone to apoptosis; British Journal of Dermatology; vol. 158; pp. 844-845; 2008.

Van Dyke, R.W.; Acidification of Lysosomes and Endosomes; Chapter 10; Sub-Cellular Biochem. 27; pp. 331-360; 1996; Plenum Oxford.

Wallmark B., et al.; Inhibition of Gastric H+,K+ -ATPase and Acid Secretion by SCH28080, a Substituted Pyridyl 1(1,2 α)imidazole; Journal of Biological Chemistry; vol. 262, No. 5; pp. 2077-2084; 1987.

Watabe, Hidenori, et al.; Regulation of Tyrosinase Processing and Trafficking by Organellar pH and by Porteasome Activity; The Journal of Biological Chem; vol. 279, No. 9; Issue of Feb. 27; pp. 7971-7981; 2004; JBC Papers in Press.

Samimi, G., et al.; Increased expression of the copper efflux transporter ATP7A mediates resistance to cisplatin, carboplatin and oxaliplatin in ovarian cancer cells. Clin Cancer Res. 2004; 10(14):4661-4669.

Samimi, G., et al.; Modulation of the cellular pharmacology of cisplatin and its analogs by the copper exporters ATP7A and ATP7B. Mol Pharmacol. 2004; 53:13-23.

Schallreuter, K.U. and Rokos, H.; From the bench to the bedside: proton pump inhibitors can worsen vitiligo; British Journal of Dermatology 2007, 156; pp. 1371-1373.

Shaefer, M., et al.; Genetic disorders of membrane transport. IV. Wilson's disease and Menkes disease. Am J Physiol. 1999; 276:G311-G314.

Thiele, D. J.; Integrating trace element metabolism from the cell to the whole organism. J Nutr. 2003; 133: 15795-15805.

Traub, L. and Kornfeld, S.; The trans-Golgi network: a late secretory sorting station; Current Opinion in Cell Biology (9) 1997; pp. 527-533.

Tumer, Z., et al.; Menkes Disease; European Journal of Human Genetics (2010) 18; pp. 511-518; 2010 Macmillan Pub.

Udelnow, A., et al.; Omeprazole Inhibits Proliferation and Modulates Autophagy in Pancreatic Cancer Cells; Plos One, www.plosone.org; vol. 6 (5) pp. 1-17; May 2011.

Voskoboinik, I., et al.; Functional analysis of the N-terminal CXXC metal-binding motifs in the human Menkes copper-transporting P-type ATPase expressed in cultured mammalian cells. J. Biol Chem. 1992; 274:22008-22012.

(56) References Cited

OTHER PUBLICATIONS

Voskoboinik, I., et al.; Functional studies on the Wilson copper P-type ATPase and toxic milk mouse mutant. Biochem Biophys Res Commun. 2001; 281: 966-970.

Wang, N., et al.; The Cotranslational Maturation of th Type I Membrane Glycoprotein Tyrosinase: The Heat Shock Protein 70 System Hands Off to the Lectin-based Chaperone System; Molecular Biology of the Cell; vol. 16; pp. 3740-3752; Aug. 2005.

Wernimont, A. K., et al.; Structural basis for copper transfer by the metallochaperone for the Menkes/Wilson disease proteins. Nat Struct Biol. 2000; 7(9):766-771.

Wikipedia; Glutathione; Feb. 17, 2012; http://en.wikipedia.org/iki/Glutathione; pp. 1-5.

Yamaguchi, Y., et al.; Biochemical characterization and intracellular localization of the Menkes disease protein. 1996; Proc. Natl Acad Sci USA; 93: 14030-14035.

Yatsunyk, L. A., et al.; Cu(I) binding and transfer by the N terminus of the Wilson disease protein. J Biol Chem. 2007; 282(12):8622-8631.

Yoshizawa, K., et al.; Copper efflux transporter (ATP7B) contributes to the acquisition of cisplatin-resistance in human oral squamous cell lines. Oncol. Rep. 2007; 18(4):987-991.

Zheng, Z., et al.; Altered microglial copper homeostasisin a mouse model of Alzheimer's disease; Journal of Neurochemistry 114 1630-1638; doi: 10.1111/j.1471-4159.2010.06888.x.

No. 2—Supplementary European Search Report; EP11732094; Completion Date: Oct. 26, 2015; Date of Mailing: Jan. 15, 2016.

\* cited by examiner

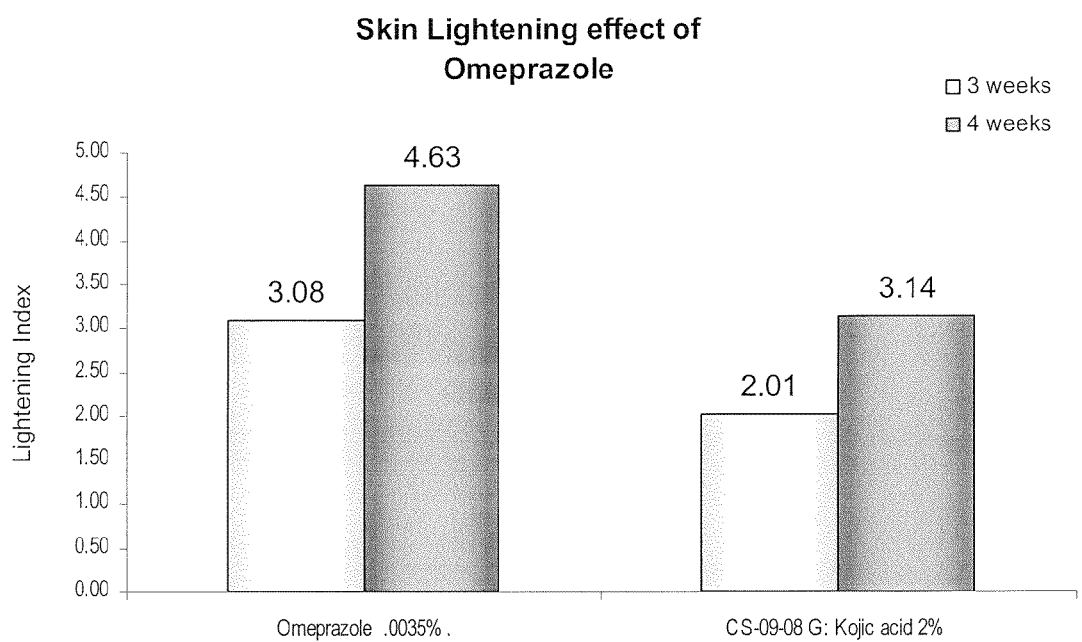

SKIN LIGHTENING COMPOSITIONS

CROSS-REFERENCE TO RELATED APPLICATIONS

The present application is a divisional application of U.S. Ser. No. 12/984,159, filed Jan. 4, 2011, and currently pending, which claims priority from U.S. Provisional Patent Application Ser. No. 61/292,577, filed Jan. 6, 2010.

BACKGROUND OF THE INVENTION

1. Technical Field

The present invention relates to novel topically applicable cosmetic and/or dermatological compositions comprising depigmenting agents for treating the skin of the face and/or body for the purposes of lightening the skin, evening skin tone and/or treating areas of hyperpigmentation. More specifically, the depigmenting agents are inhibitors of Type I H+, K+-ATPases.

2. Description of the Prior Art

Consumers of skin lightening products spend more than $1 billion annually in search of Skin with an even tone on their faces, hands and bodies. The development of areas of hyperpigmentation on the skin is obviously of great concern to these individuals. The hyperpigmented areas are caused by a concentration of melanin in the keratinocytes located at or near the skin surface. Melanin pigment is produced in melanocytes in highly specialized organelles known as melanosomes. Melanocytes are found in several locations throughout the body, including in the bottom layer of the skin's epidermis, the iris of the eye and the hair. Manufacturing of melanin begins when melanin-making enzymes are activated and transform the amino acid tyrosine to intermediates of the end product, melanin. The actual production of melanin begins in the melanosomes. Inside human melanosomes, a series of chemical reactions, catalyzed by enzymes, converts tyrosine into two types of melanin, eumelanin, which is brown or black in color, and pheomelanin, which is red or yellow. The mechanism of formation of melanin includes the following principal mechanisms:

derivatives. Hydroquinone also competes for tyrosine oxidation in active melanocytes. Although highly efficacious as depigmenting agents, the use of these compounds, in view of their cytotoxicity, is legally limited to a concentration of 2% without a prescription in the U.S., and is not available over the counter elsewhere. Examples of other depigmenting agents include kojic acid, which chelates the copper ion in the active site of tyrosinase; but which tends to be unstable in the processing of cosmetics; hydrogen peroxide, which inhibits melanogenesis because it bleaches the melanin but which is unstable; ascorbic acid, which converts dopaquinone back to dopa, but which has low activity and low stability; salicylic acid and lactic acid, which increase cell turnover; and unsaturated fatty acids, such as linoleic acid, which affect the processing and function of tyrosinase in connection with the ubiquitin-proteasome pathway.

Other depigmenting agents include those which interfere with one or more steps in the production of melanin. These agents may act by inhibiting one or more enzymes (e.g. tyrosinase) involved in melanogenesis or by inserting themselves in the synthetic chain as a structural analogue of one of the chemical compounds. Still other depigmenting agents may act by disrupting tyrosinase processing and sorting through the secretory pathway (translocation through membrane-bound organelles, e.g., endoplasmic reticulum→Golgi→endosomes→melanosomes in melanocytes). A further depigmenting mechanism could involve the modulation of tyrosinase messenger RNA (mRNA) transcription and its post-transcriptional stability. Depigmenting agents may also act by decomposing already formed melanin.

During routine screening of compounds for inhibition of melanogenesis in cultured B16F10 mouse melanoma cells, it was unexpectedly discovered by the inventors that a class of compounds called substituted benzimidazoles all strongly inhibited melanogenesis. This was quite surprising since the only activity known for these compounds is the specific inhibition of the proton pump protein reportedly only found in the apical cytoplasmic membrane of gastric parietal cells (Olbe, L., Carlsson E., Lindberg P. A Proton-Pump Inhibitor Expedition: The Case Histories of Omeprazole and Esomeprazole,

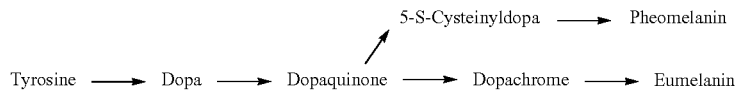

Tyrosinase is the essential enzyme involved in this reaction sequence. It catalyzes the conversion of tyrosine into dopa (dihydroxyphenylalanine) and the conversion of dopa into dopaquinone.

Once the melanosomes are loaded with melanin, the melanosomes are transported along a secretory pathway to their final destination in keratinocytes, which are barrier cells in the uppermost layer of the skin, and into the hair, and to other locations in the body. The amount of melanin transported and the mix of the pigments determines skin, eye and hair color in humans. Melanin functions to protect DNA in skin cells by absorbing ultraviolet radiation which can damage the DNA, and leave the skin vulnerable to cell damage, including sunburn, premature aging and skin cancer.

Various depigmenting agents having differing mechanisms of action and levels of efficacy are known. Depigmenting agents may act directly on epidermal melanocytes, such as by destroying these cells. One such agent is hydroquinone and its

*Nature Reviews Drug Discovery*, 2:132-9, 2003). The gastric proton pump has never been found in melanocytes and the inventors were unable to detect its gene expression in melanocytes. Another gastric proton pump inhibitor, a substituted imidazopyridine compound with a different reactive site, was tested and it also surprisingly inhibited melanogenesis. This led the inventors to consider, for the first time, using gastric proton pump inhibitors to depigment skin.

Recent studies have suggested that differences in epidermal pigmentation may be due to differences in melanosomal pH. However, the literature has been contradictory as to whether melanogenesis is favored by acidic or basic pH. On the one hand, it has been observed that melanosomes are normally acidic (Brilliant, M. and Gardner, Melanosotnal pH, Pink Locus Protein and their Roles in Melanogenesis, *J. of Invest. Dermatol.* 117(2) 2001; Moellmann, G., Slominski, A., Kuklinska, E., Lerner A. B.: Regulation of Melanogensis in Melanocytes. *Pigment Cell Res.*, 1:79-87, 1988; Bhatnagar, V., Anjaiah, S. Puri, N, Arudhra Darshanam, B. N., and Ramaia, A.: pH of Melanosomes of B16 Murine Melanoma is Acidic: Its Physiological Importance in the Regulation of Melanin Biosynthesis, *Arch. Biochem. Biophys.* 307:183-192, 1993; Ramaiah, A.: Lag Kinetics of Tyrosinase: Its Physiologic Implications, *Indian J. Biochem. and Biophys.* 33:349-356, 1996), and that the acidification of various intracellular compartments is important for a number of processes (Van Dyke, R. W.: Acidification of Lysosomes and Endosomes, *Sub-Cellular Biochem.*, 27:331-360, 1996; Grabe, M. and Oster, G.: Regulation of Organelle Acidity, *J. General Physiol.* 117:329-344, 2001). Devi et al. proposed that since melanosomes can be acidic, low melanosomal pH facilitates melanogensis, and therefore tyrosinase activity is optimal at acidic pH and inactive at neutral pH (Devi, C. C., Tripathi R. K., Ramaia, A, pH-dependent Interconvertible Allosteric Forms of Murine Melanoma Tyrosinase: Physiological Implications. *Eur. J. Biochem.* 166:705-711, 1987). Very recently, Gunathilake, et al. reported that melanocytes, and particularly the dendrites, from darkly pigmented subjects are significantly more acidic than those from lightly pigmented subjects, and that this acidity appears to be localized to melanosomes (Gunathiliake R., Schurer N., Shoo B., Celli, A., Hachem J. P., Curmrine D., Sirimanna, G., Feingold K., Mauro t., Elias P.: pH-regulated Mechanism Accounts for Pigment-Type Differences in Epidermal Barrier Function. *J. Invest. Dermatol*, 129:1719-1729, 2009). On the other hand, other groups have observed that mammalian tyrosinase has optimal enzymatic activity at near neutral pH and that its activity is lost with decreasing pH (Hearing, V. J. and Ekel, T. M.: Mammalian Tyrosinase. A Comparison of Tyrosine Hydroxylation and Melanin Formation, *J. Biochem.*, 157: 549-557, 1976; Saeki, H. and Oikawa, A.: Stimulation of Ionophores of Tyrosinase Activity of Mouse Melanoma Cells in Culture, *J. Investig. Dermatol.* 85:423-425, 1985; Townsend, D., Guillery, P., and King. R. A.: Optimized Assay for Mammalian Tyrosinase (Polyphenol Phenyloxidase), *Anal. Biochem.* 139:345-352, 1984). Ancans et al., reported that near neutral melansomal pH is optimal for human tyrosinase activity, melanogenesis and maturation rate of melanosomes, and that low pH suppresses melanin production in Caucasian melanocytes. It was further observed that the ratio of eumelanin/phaeomelanin production and the maturation rate of melanosomes are regulated by melanosomal pH, and that therefore, melanosomal pH appears to be an essential factor which regulates multiple stages of melanin production (Ancans, J, D., Tobin, J., Hoogdujin, J. J. Smit, N. P., Wakamatsu, K., and Thody, A. J.: Melanosomal pH Controls Rate of Melanogenesis, Eumelanin/Phaeomelanin Ratio and Melanosome Maturation in Melanocytes and Melanoma Cells, *Experimental Cell Research* 268:26-35, 2001). Studies by Smith et al. also suggested that the internal pH of melanosomes in Caucasians is acidic, and at this pH tyrosinase is inactive, while the pH of melanosomes of Blacks appears to be more neutral and optimal for tyrosinase activity (Smith et al.: The Relationship Between Na+/H+ Exchanger Expression and Tyrosinase Activity in Human Melanocytes. *Exptl. Cell Res.* 298:521-534, 2004). Thus, there is disagreement in the literature as to the role of melanosome pH in the production of melanin.

Puri et al. reported the aberrant pH of mouse "p" gene (pink-eyed dilution (p) mutant) melanocytes, and, based on a finding of fewer acidic melanosomes, hypothesized that the p protein functions in the acidification of melanosomes, e.g., an ion-exchange or channel protein, in the melanosomal membrane, which may affect the activity and/or routing of tyrosinase (Puri, N., Gardner, J. M., Brilliant, M. H.: Aberrant pH of Melanosomes in Pink-eyed Dilution (p) Mutant Melanocytes. *Soc. Invest. Dermatol.* 115:607-613, 2000). Ancans et al. suggested alternative hypotheses to Puri, since p-protein does not utilize energy from ATP which would enable it to function as an ionic transporter against a proton gradient. Ancans et al. treated mutant and wild-type melanosomes with v-type proton pump inhibitors (responsible for organelle acidification), and observed that, in mutant cells, neutralization resulted in increased melanin content, while there was no significant change in the wild-type cells. The study suggested that P-locus protein has a role in creating a near neutral local microenvironment and that this change facilitates tyrosinase activity. Thus, p-locus protein may function as a channel to reduce the proton concentration inside the melanosome analogous to Na+/H+ antiporters (NHEs), (Ancans, J., Hooduijn, J., Thody, A. J.: Melanosomal pH, Pink Locus Protein and their Roles in Melanogenesis. *J. Invest. Dermatol.* 117 (1):158-159, 2001). Halaban et al., suggested that bafilomycin A1 and monensin play dual roles in the processing of tyrosinase: reduction of levels of tyrosinase retained in the endoplasmic reticulum and facilitating the release of tyrosinase from the endoplasmic reticulum to the Golgi by increasing the pH in either the endoplasmic reticulum or the endoplasmic reticulum-Golgi intermediate compartment (Halaban, R., Patton, R. S., Cheng, E., Svedine, S., Trombetta, E. S., Wahl, M. L., Arujan, S. and Hebert, D. N.: Abnormal Acidification of Melanoma Cells Induces Tyrosinase Retention in the Early Secretory Pathways, *J. Biol. Chem.* 277(17):14821-14828, 2002).

Thus there is no clear guidance from the literature as to whether increasing or decreasing the pH of acidic organelles including melanosomes would benefit depigmentation. Even if one hypothesized that agents which inhibit the neutralization of pH in melanocytes might be desirable, prior to the present invention, there was no recognized means by which to reduce the pH of the acidic organelles, and therefore, certainly none that were safe. The available pH adjusting compounds such as bafilomycin A1 and monensin increase the pH of acidic organelles, and the known target for the gastric proton pump inhibitors is not present in melanocytes.

SUMMARY OF THE INVENTION

This invention relates to safe and effective compounds and compositions which achieve skin lightening or depigmenting in skin, and to their methods of use.

Specifically, the invention relates to compositions comprising a skin lightening or depigmenting effective amount of at least one compound represented by the structural formula:

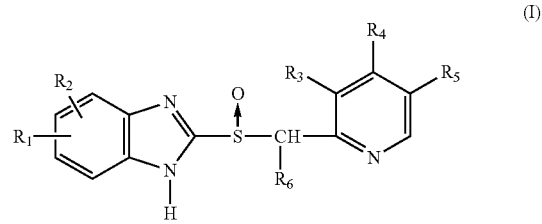

wherein:

$R_1$ and $R_2$ are same or different and are each selected from the group consisting of hydrogen, alkyl, carbomethoxy, carboethoxy, alkoxy, and alkanoyl, any of which may be halogen-substituted, and halogen;

$R_6$ is selected from the group consisting of hydrogen, methyl, and ethyl; and $R_3$, $R_4$ and $R_5$ are the same or different and are each selected from the group consisting of hydrogen, methyl, methoxy, ethoxy, methoxyethoxy, ethoxyethoxy, propoxy, propoxymethoxy, and the like, any of which may be halogen-substituted;

or a derivative or physiologically acceptable salt, solvate or bioprecursor, or stereoisomer or enantiomer thereof; or by the structural formula:

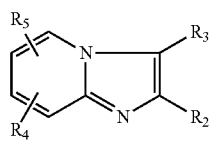

(II)

wherein:

$R_2$ is hydrogen, lower alkyl or hydroxy lower alkyl;

$R_3$ is lower alkyl, —$CH_2CN$, hydroxy lower alkyl, —NO, —$CH_2N$=C or

(wherein $R_6$ and $R_7$ are independently selected from the group consisting of hydrogen and lower alkyl) or hydrogen provided $R_2$ is not hydrogen;

$R_4$ is Z-T-W wherein Z represents —O—, —NH— or a single bond; T represents a straight- or branched-chain lower-alkylene group; when Z is a single bond, T also represents an ethenylene or a propenylene group wherein the unsaturated carbon is at the single bond; when Z is —O—, T also represents an allylene group wherein the saturated carbon is at the oxygen; and W represents hydrogen, when T is allylene and Z is —O—, and Ar, wherein Ar is selected from thienyl, pyridinyl, furanyl, phenyl and substituted phenyl wherein there are one or more substituents on the phenyl independently selected from halogen or lower alkyl; and $R_5$ is hydrogen, halogen or lower alkyl;

or a derivative or physiologically acceptable salt, solvate or bioprecursor, or stereoisomer or enantiomer thereof;

formulated into a topically applicable, cosmetically or dermatologically acceptable vehicle, carrier or diluent therefor.

Included in this invention are pharmaceutically-, cosmetically- and dermatologically-acceptable salts of the above compounds, stereoisomers and enantiomers thereof free from or mixed with other enantiomers or stereoisomers and such compounds in compositions with a cosmetically-, dermatologically- or pharmaceutically-acceptable carrier thereof.

This invention further relates to methods of lightening or depigmenting skin by administering to the skin in need thereof a composition comprising a safe and effective amount of a skin lightening or depigmenting active as described herein.

The compositions of the invention may consist essentially of the skin lightening or depigmenting active compound. By "consisting essentially of", it is intended that the compositions of the invention do not include any component which would adversely affect the desired properties imparted to the compositions by the active skin lightening or depigmenting compound.

As used herein, the term "topical application" means directly layering on or spreading on outer skin.

As used herein the term "cosmetically or dermatologically acceptable" means suitable for use in contact with skin without undue toxicity, incompatibility, instability, irritation, allergic response, and the like, commensurate with a reasonable benefit/risk ratio.

As used herein, the term "hyperpigmented region" means a localized region of the skin having high melanin content.

As used herein, the term "skin-lightening" or "skin depigmenting" means decreasing melanin in skin, including overall lightening of skin tone and lightening of hyperpigmented regions, including age spots, melasma (chloasma), freckles, post-inflammatory hyperpigmentation or sun-induced pigmented blemishes, and the like.

As used herein the term and "safe and effective skin-lightening/depigmenting amount" means an amount of compound or composition sufficient to significantly induce a positive modification in the condition to be treated (i.e., lightening skin or evening skin tone), but low enough to avoid serious side effects.

As used herein the term "derivative" means physiologically acceptable salt, solvate or bioprecursor thereof, and the like.

BRIEF DESCRIPTION OF THE DRAWING

The FIGURE is a graph illustrating the skin lightening effect of a composition of the invention as compared with a positive control.

DETAILED DESCRIPTION OF THE INVENTION

Inhibitors of gastric acid secretion can be classified into two general categories based on their site of action; inhibitors working at the basolateral membrane of the gastric parietal cell, such as histamine $H_2$-receptor antagonists or anticholinergic agents, and those working at the secretory membrane, such as inhibitors of the Type I K+/H+-ATPase, also known as the proton pump or p-pump of the parietal cell. The p-pump inhibitors include reversible and irreversible types. Recently, the substituted benzimidazoles, agents belonging to the latter class, have received much attention.

Certain substituted benzimidazole compounds are generally known as gastric acid inhibitors or gastroesophageal reflux disease (GERD) and ulcer medications. They are also referred to as proton pump inhibitors or PPIs. PPI products currently on the market include omeprazole, 5- or 6-methoxy-2-{[(4-methoxy-3,5-dimethylpyridin-2-yl)methyl]sulfinyl}-1H-benzimidazole; esomeprazole, S-5-methoxy-2-{(4-methoxy-3,5 dimethylpyridin-2-yl)methylsufinyl]-3H-benzoimidazole; lansoprazole, 2-{[3-methyl-4-(2,2,2-trifluoroethoxyl)pyridin-2-yl]methylsulfinyl-1H-benzo(d)imidazole; pantoprazole, RS-6-(difluoromethoxy))-2-[(3,4-dimethoxypyridin-2-yl)methylsulfinyl]-1H-benzo(d)imidazole; and rabeprazole (pariprazole), 2-([4-(3-methoxypropoxy)-3-methylpyridin-2-yl]methylsulfinyl)-1H-benzo(d)imidazole. The PPIs are safe and have been observed to be more effective in reducing stomach acid than the $H_2$-receptor blockers. A particularly popular PPI is omeprazole, also known as Prilosec®. Other PPIs include leminoprazole, 2-((o-(isobutylmethylamino)benzyl)sulfinyl)benzimidazole; and timoprazole, 2-(pyridine-2-ylmethylsulfinyl)-1H-benzimidazole.

All of these PPI compounds contain a basic structural framework and differ only in the nature of substituents placed on the pyridine and benzimidazole rings as shown by the following formula:

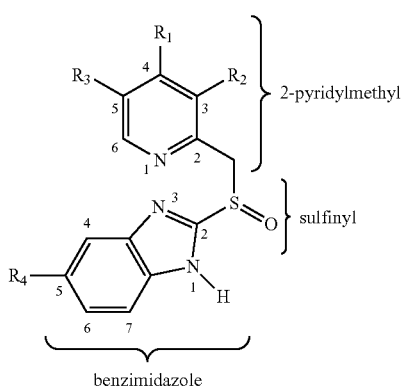

benzimidazole

Commonly used PPIs are shown by the following formulas:

Benzimidazoles

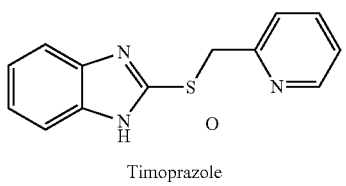

Timoprazole

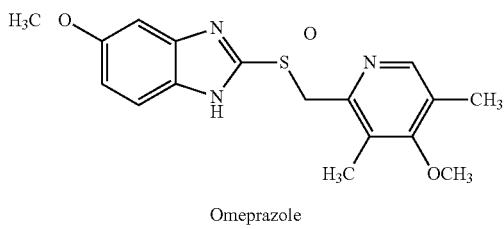

Omeprazole

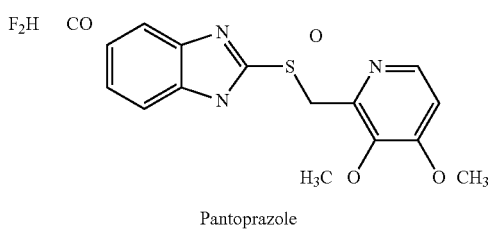

Pantoprazole

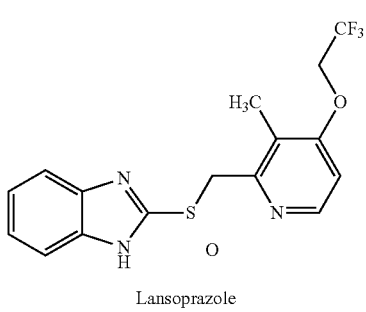

Lansoprazole

-continued

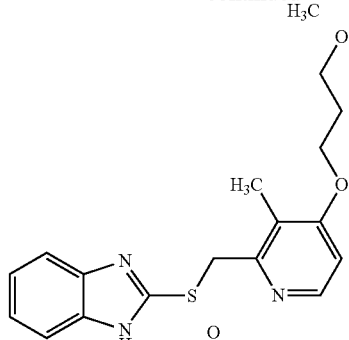

Rabeprazole

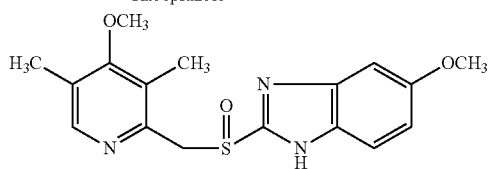

Esomeprazole

The PPIs are compounds that block the gastric hydrogen potassium ATPase or H+/K+-ATPase, the enzyme primarily responsible for the acidification of the stomach contents. This ATPase is found in parietal cells which are highly specialized epithelial cells in the inner cell lining of the stomach. This ATPase moves acid across the gastric mucosa and gastric parietal cells (Chang, H., Saccomani G., Rabon, E., Schackmann R., Sachs, G.: Proton Transport by Gastric Membrane Vesicles, *Biochim et Biophysica Acta,* 464(2):313-327, 1977; Sachs G. and Wallmark, B., The Gastric H+K+ ATPase: The Site of Action of Omeprazole. *Scand. J. of Gastroenterol.,* 24:No. s166, 3-11, 1989). Parietal cells possess a secretory membrane system and the H+/K+-ATPase is the major protein constituent of these membranes. The ATPase undergoes a cycle of phosphorylation and dephosphorylation coupled to the outward movement of H+ (from the cytoplasm of the parietal cell) and the inward movement of K+ (from the gastric lumen) in a net electroneutral fashion. The ATPase functions as an ion pump to transport ions against a concentration gradient using energy derived from the hydrolysis of ATP. As with all p-type ATPases, a phosphate group is transferred from adenosine triphosphate (ATP) to the H+/K+-ATPase during the transport cycle. The phosphate transfer powers a conformational change in the enzyme that helps drive ion transport. The PPIs act by irreversibly blocking the H+, K+-ATPase (Robinson, M. and Horne, J.: Clinical Pharmacology of Proton Pump Inhibitors: What the Practicing Physician Needs to Know, *Drugs:* 63:2739-2754, 2003), thereby inhibiting the secretion of acid into the stomach. These anti-secretory compounds specifically inhibit the ATPase at the secretory surface of the gastric parietal cell, blocking the final step of acid production.

Unlike $H_2$-antagonist compounds that interact competitively and reversibly with $H_2$ receptors, the PPI, in the acidic environment of the stomach, forms a covalent disulfide bond with the ATPase enzyme, leading to an irreversible inhibition of the pump. One sulfur atom in the disulfide bond will come from a cysteine residue (CYS) on the ATPase and the other will come from the PPI. CYS813 has been identified as the residue most critical to the inhibiting action of the PPIs. This cysteine is located in the luminal vestibule of the ATPase and is accessible from the extracytoplasmic area of the ATPase protein. Some PPIs also will react with CYS822. Additional residues on the enzyme are also important for holding and positioning the PPI in place. (Roche, V. F.: The Chemically Elegant Proton Pump Inhibitors, *Amer. J. Phar. Educ,* 70(5) Article 101, 2006; Qaisi, A. M., Tutunji, J. F., Tutunji, L. F.: Acid Decomposition of Omeprazole in the Absence of Thiol: a Differential Pulse Polarographic Study at the Static Mercury Drop Electrode (SMDE), *J. Pharm. Sci.* 95(2):384-391, 2006). The PPI must be activated to bind with the ATPase; that is, the PPI requires an acidic environment to undergo the re-arrangement to the active form. As shown in the scheme below, the activation pathway begins with two protonation reactions which readily occur immediately outside the highly acidic parietal cell. The sulfonamide (protonated) form of the PPI binds to thiol groups within the alpha subunit of the ATPase to form relatively stable disulfides. (Besancon, M., Shin, J. M., Mercier, F., Munson, K., Miller, M., Hersey, S., Sachs, G.: Membrane Topology and Omeprazole Labelling of the Gastric H+, K(+) Adenosinetriphosphatase. *Biochem.* 32(9):2345-2355, 1993; Besancon, M., Simon, A., Sachs, G., Shin, J. M.: Sites of Reaction of the Gastric H, K-ATPase with Extracytoplasmic Thiol Reagents. *J. of Biol. Chem.* 272:22438-446. 1997).

prazole sulfide, lansoprazole sulfide, pantoprazole sodium salt, and the like, and imidazopyridines, such as SCH-28080 and structurally related compounds, could be of value for evening skin tone. An ideal compound for this purpose should be readily deliverable into the skin, stable, have a therapeutic index of $IC_{50} < LD_{50}$ by a factor of 1,000, and demonstrate long-lasting results.

The PPIs were initially discovered by the inventors to be modulators of melanin synthesis during a high throughput screening of indoles and imidazoles. B16F10 melanoma cells were incubated for three days with test compounds at various concentrations. The cells were fixed, dried and solubilized, and the melanin content was determined. Based on the melanin content of the cells, it was observed that one of the compounds most potent in reducing melanin in the cells was omeprazole. It was then determined that omeprazole inhibits melanin synthesis without cytotoxicity in B16F10 melanoma cells, normal human melanocytes and 3-D skin (NHEK and melanocytes). Further experiments using Black, Asian and Caucasian melanocytes showed that omeprazole at 12.5, 25 and 50 µg/ml reduced melanin production by about 50%, 30%, and 20%, respectively.

Additionally, the present inventors have observed that omeprazole creates a more acidic environment in melano-

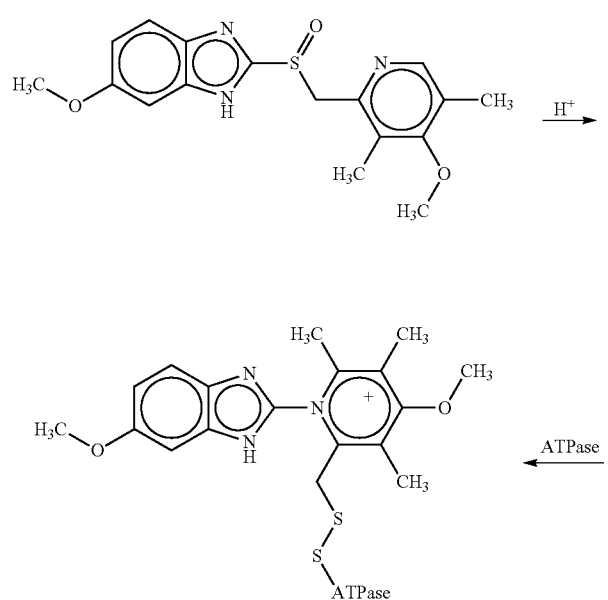
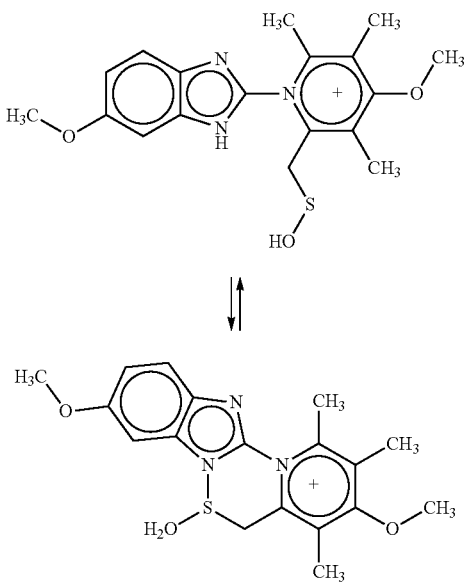

The reversible type proton pump inhibitors are the APAs (acid pump antagonists), also, but less accurately, referred to as P-CABs (potassium competitive acid blockers), since not all APAs will be strictly potassium competitive. The major classes of these reversible inhibitors include imidazopyridine derivatives, acyl quinoline derivatives and pyrrolopyridazine derivatives.

Since pH is an important factor in melanogenesis, and consumers desirous of an even skin tone are always looking for more efficacious and safe products, the present inventors investigated whether inhibitors of Type I H+, K+-ATPases, such as, substituted-benzimidazoles, including the 2-pyridyl-methylsulfinyl-benzimidazoles, such as omeprazole, and structurally related compounds, including esomeprazole, lansoprazole, pantoprazole, and rabeprazole, and analogues or derivatives thereof, for example, omeprazole sulfide, pantocytes. The protocol to detect changes in pH followed that of Cheli, Y. et al. B16F10 melanoma cells were seeded in glass bottom dishes and maintained in DMEM medium with 10% FBS. Test compounds, omeprazole or forskolin (which creates a more alkaline environment and induces melanin production) were added 18 hours after seeding and changes in pH were assessed after either 4 or 24 hours. Cells were washed with fresh culture medium and incubated for 20 minutes in the presence of 30 µM DAMP ([3-(2,4-dinitroanilino) 3'amino-N-methyldipropylamine], a weak base which accumulates in acidic compartments). Cells were fixed in 3% PFA for 20 minutes at room temperature. The glass bottom dishes were washed with PBS, incubated 10 minutes in $NH_4Cl/PBS$ at room temperature and permeabilized in PBS with 0.1% Triton-100 for two minutes on ice. The dishes were then incubated with a green reflecting fluoroscein isothiocyanate (FITC)-labeled rabbit anti-dinitrophenyl (DNP) antibody (1/50 PBS plus 1% BSA) for one hours at 37° C. The intensity of fluorescence indicated the accumulation of DAMP. Increased intensity of the fluorescence can be related to lowered pH. (Cheli, Y., Luciani, F., Khaled, M., Beuret, L., Billie, K., Gounon, Pl, Ortonne, J. P., Bertolotto, C., and Ballotti, R. Alpha-MSH and cyclic-AMP elevating agents control melanosome pH through a PKA-independent mechanism. *J. Biol. Chem.*, 284:18699-18706, 2009). The data are shown in Table I below.

TABLE I

EFFECT OF OMEPRAZOLE ON THE PH OF MELANOCYTES

| Conditions | Average fluorescence per cell ± S.D. |
|---|---|
| 24 hour incubation | |
| Control | 110.3 ± 8 |
| Omeprazole 50 μM | 139.3 ± 14.4 |
| Forskolin 20 μM | 87 ± 15.1 |
| 4 hour incubation | |
| Control | 72.5 ± 31.3 |
| Omeprazole 50 μM | 145.5 ± 14.5 |
| 4 hour incubation | |
| Control | 89 ± 23 |
| Omeprazole 25 μM | 124.3 ± 2.5 |
| Omeprazole 50 μM | 133.7 ± 13.3 |

Fluorescence intensity increased after exposure of cells for 24 hours to omeprazole, indicating that a more acidic pH was induced. On the other hand, treatment with forskolin decreased DAMP labeling. It has been previously shown that forskolin induces an alkalinization of the melanosome milieu. Additionally, the data show that the acidification occurs relatively rapidly, as the intensity of fluorescence is significantly increased after only 4 hours. Concentrations of 25 μM and 50 μM omeprazole are both effective at lowering the pH of melanoma cells after 4 hours of treatment. This shorter time period would be expected if omeprazole acted through direct inhibition of a proton pump rather than through some indirect effect requiring, for example, protein synthesis of the pump enzyme.

A further unexpected discovery by the inventors was that the compound SCH-28080 inhibited melanogensis in a manner equally as efficient as omeprazole. SCH-28080, [2-methyl-8-(phenylmethoxy)imidazo(1,2a)pyridine-3-acetonitrile], having the formula shown below, is a hydrophobic amine in the class of imidazopyridine derivatives, more specifically, substituted pyridyl 1 [1,2-a]imidazoles, a class which also includes SCH-32651, [3-amino-2-methyl-8-phenylmethoxyimidazo[1,2-a]pyrazine HCl]. SCH-28080 is similar to omeprazole in that it is a proton pump inhibitor, but it is distinct from omeprazole and its derivatives in chemical structure, particularly in that it completely lacks a sulfur moiety. Its effects on the gastric $H^+$, $K^+$-ATPase are also completely different. SCH28080 is a competitive inhibitor of the $K^+$ binding site and therefore its inhibition is reversible (Wallmark B., C. Briving, J. Fryklund, K. Munson, R. Jackson, J. Mendlein, E. Rabon, G. Sachs, Inhibition of Gastric $H^+$,$K^+$-ATPase and Acid Secretion by SCH28080, a Substituted Pyridyl 1(1,2α)imidazole. *J. Biol. Chem.* 262:2077-2084, 1987; Beil, et al., W., Hatchbarth, I, Sewing, K. F.: Mechanism of Gastric Antisecretory Effect of SCH 28080, *Br. J. Pharmac.* 88:19-23, 1986), while omeprazole makes a covalent, irreversible bond. The target site is also different. SCH-28080 targets the glutamine at position 822 of the gastric pump (Asano S., S. Matsuda, Y. Tega, K. Shimizu, S. Sakamoto, N. Takeguchi, Mutational Analysis of Putative SCH28080 Binding Sites of the Gastric $H^+$,$K^+$-ATPase, *J. Biol. Chem.* 272, 17668-17674, 1997) while omeprazole reacts with cysteines at other positions in the protein.

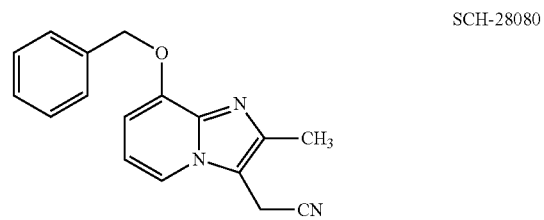 [SMILES: Cc1nc2c(OCc3ccccc3)cccn2c1CC#N]

SCH-28080

Other compounds in the class of imidazopyridine derivatives include, but are not limited to, soraprazan [(7R,8R,9R)-2,3-dimethyl-8-hydroxy-7(2-methoxyethoxy)-9-phenyl-7,8,9,10-tetrahydro-imidazo-[1,2-h][1,7]-naphthyridine], pumaprazole 8-(2-methoxycarbonylamino-6-benzulamino)-2,3-dimethylimidazo-[1,2-a)pyridine-D,L-hemimalate, AR-H047108, (8-[(2-ethyl-6-methylbenzyl)amino]2,3-dimethylimidazo[1,2-a]pyridine-6-carboxamide; dapiprazole, 3-{2-[4-(2-methylphenyl)piperazin-1-yl]ethyl}-5,6,7,8-tetrahydro-[1,2,4]triazolo[4,5-a]pyridine; AZD0865, ((8-[2,6-dimethylbenzyl)amino]-N-(2-hydroxyethyl)-2,3-dimethylimidazo[1,2-a]pyridine-6-carboxamide; and tenatoprazole, 3-methoxy-8-[(4-methoxy-3,5-dimethyl-pyridin-2-yl)methylsulfinyl]-2,7,9-triazabicyclo[4.3.0]nona-2,4,8,10-tetraene. It is of interest to note that tenatoprazole, shown below, contains a sulfinyl moiety and is therefore also structurally related to the substituted benzimidazoles. Its inhibition is resistant to reversal.

Imidazopyridine

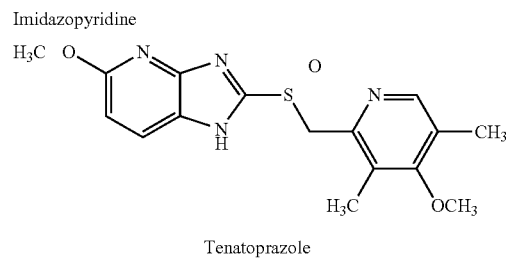

Tenatoprazole

Acyl quinoline derivatives include, but are not limited to, the compounds aripiprazole, 7-[4-[4-(2,3-dichlorophenyl)piperazin-1-yl]butoxy]-3,4-dihydro-1H-quinolin-2-one and revaprazan, [5,6-dimethyl-2-(4-fluorophenylamino)-4-(1-methyl-1,2,3,4-tetrahydroisoquinolin-2-yl-pyrimidine], shown below.

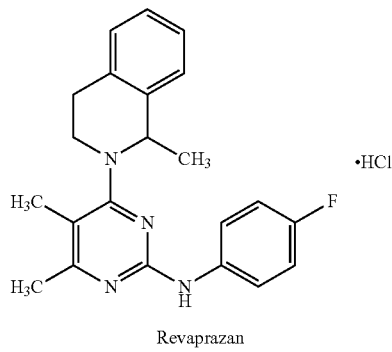 [SMILES: Cc1nc(Nc2ccc(F)cc2)nc(N2CCc3ccccc3C2C)c1C ; Cl]

Revaprazan

Pyrrolopyridazine derivatives include, but are not limited to, CS-526, 7-(4-fluorobenzyloxy)-2,3-dimethyl-1-{[(1S,2S)-2-methylcyclopropyl]methyl}-1H-pyrrolo[2,3-d]pyridazine, shown below.

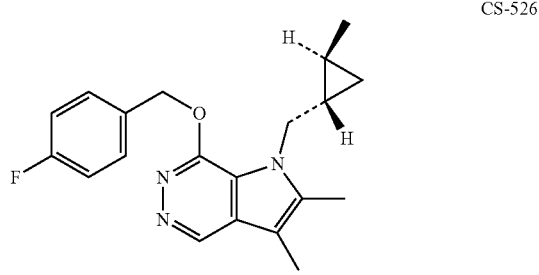 [SMILES: Cc1c(C)n(C[C@H]2C[C@@H]2C)c2c(OCc3ccc(F)cc3)nncc12]

CS-526

Despite these differences, there are clear similarities among the reversible and irreversible proton pump inhibitors that highlight the invention. First, they are weak bases, which would lead to their accumulation at sites of relative acidity. Second, they react with the acidic side of the $H^+$, $K^+$-ATPase, which in the case of the gastric pump is in the lumen of the stomach. Third, they are effective inhibitors of only the Type I $H^+$, $K+$-ATPases, which are all resistant to ouabain, and which are distinct from Type III $H^+$, $K^+$-ATPases, such as ATP12A found in bladder and colon, which are sensitive to ouabain, resistant to SCH-28080 and which have an aspartic acid residue at the position corresponding to the glutamine residue in the Type I $H^+$, $K^+$-ATPases.

Because both omeprazole (and its analogues and structurally related compounds) and SCH-28080 inhibit melanogenesis despite their differences in structure and mechanisms of action, this leads to the novel generalization that inhibitors of Type I $H^+$, $K^+$-ATPases are also inhibitors of melanogenesis.

The invention is described hereinbelow in greater detail with reference to its preferred embodiments. These embodiments, however, are set forth to illustrate the invention and are not to be construed as a limitation thereof, the invention being defined by the claims.

In one aspect, the invention relates to a composition for topical application to skin, comprising a skin-lightening/depigmenting effective amount of at least one compound or derivative thereof which is an inhibitor of Type I H+, K+-ATPases.

In one preferred embodiment of the first aspect, the invention relates to a composition for topical application to skin, comprising a skin-lightening/depigmenting effective amount of at least one compound represented by the structural formula:

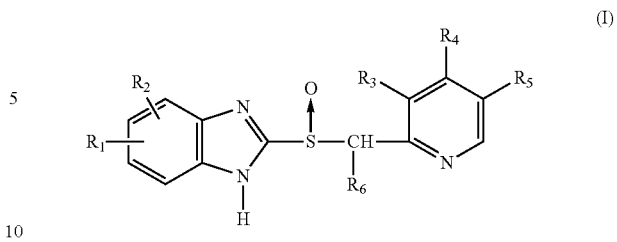

(I)

wherein:

$R_1$ and $R_2$ are same or different and are each selected from the group consisting of hydrogen, alkyl, carbomethoxy, carboethoxy, alkoxy, and alkanoyl, any of which may be halogen-substituted and halogen;

$R_6$ is selected from the group consisting of hydrogen, methyl, and ethyl; and $R_3$, $R_4$ and $R_5$ are the same or different and are each selected from the group consisting of hydrogen, methyl, methoxy, ethoxy, methoxyethoxy, ethoxyethoxy, propoxy, propoxymethoxy, and the like, any of which may be halogen-substituted;

or a derivative or physiologically acceptable salt, solvate or bioprecursor, or stereoisomer or enantiomer thereof;

formulated into a topically applicable, cosmetically or dermatologically acceptable vehicle, carrier or diluent therefor.

Alkyl $R_1$ and $R_2$ of formula I are suitably alkyl having up to 7 carbon atoms, preferably up to 4 carbon atoms. Thus, alkyl R may be methyl, ethyl, n-propyl, isopropyl, n-butyl or isobutyl, whether or not halogen-substituted.

Halogen $R_1$ and $R_2$ are chloro, bromo, fluoro, or iodo.

Alkoxy $R_1$ and $R_2$ are suitably alkoxy groups having up to 5 carbon atoms, preferably up to 3 carbon atoms, such as methoxy, ethoxy, n-propoxy, or isopropoxy, whether or not halogen-substituted.

Alkanoyl $R_1$ and $R_2$ have preferably up to 4 carbon atoms and are e.g. formyl, acetyl, or propionyl, preferably, acetyl, whether or not halogen-substituted.

One preferred group of compounds of the general formula I are those wherein $R_1$ and $R_2$ are the same or different and are each selected from the group consisting of hydrogen, alkyl, and alkoxy, whether or not halogen-substituted, $R_6$ is selected from the group consisting of hydrogen, methyl, and ethyl, and $R_3$, $R_4$, and $R_5$ are the same or different and are each selected from the group consisting of hydrogen, alkyl and alkoxy, whether or not substituted by halogen.

A second preferred group of compounds of the general formula I are those wherein $R_1$ and $R_2$ are the same or different and are each selected from the group consisting of hydrogen, methyl, methyl substituted by halogen, methoxy, and methoxy substituted by halogen, $R_6$ is hydrogen, $R_3$, $R_4$, and $R_5$ are the same or different and are each selected from the group consisting of hydrogen, methyl, ethyl, propyl, methoxy, ethoxy, propoxy, methoxymethoxy, ethoxyethoxy, propoxypropoxy, methoxyethoxy, ethoxymethoxy, methoxypropoxy, propoxymethoxy, ethoxypropoxy, propoxyethoxy, whether or not substituted by halogen.

Non-limiting examples of preferred compounds are those in which R1 and R2 are each hydrogen or methoxy, R3 and R5 are methyl and R4 is methoxy; in which $R_1$, $R_2$, $R_5$ and $R_6$ are hydrogen, $R_3$ is methyl and $R_4$ is propoxymethoxy; in which $R_1$, $R_2$, $R_3$, $R_4$, $R_5$ and $R_6$ all are hydrogen; in which $R_1$, $R_2$, $R_5$ and $R_6$ all are hydrogen, $R_3$ is methyl and $R_4$ is ethoxy substituted by halogen; and in which $R_1$ and $R_2$ are hydrogen or methoxy substituted by halogen, $R_6$ is hydrogen, $R_3$ is hydrogen and $R_4$ and $R_5$ are methoxy.

Most preferred for use in the compositions of the present invention are omeprazole, its derivatives and analogues.

A further preferred embodiment of the first aspect of the present invention relates to a composition for topical application to skin, comprising a skin-lightening/depigmenting effective amount of at least one compound represented by the structural formula:

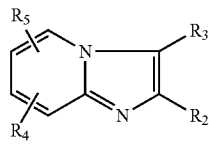
(II)

wherein:

$R_2$ is hydrogen, lower alkyl or hydroxy lower alkyl;

$R_3$ is lower alkyl, —$CH_2CN$, hydroxy lower alkyl, —NO, —$CH_2N$=C or

(wherein $R_6$ and $R_7$ are independently selected from the group consisting of hydrogen and lower alkyl) or hydrogen provided $R_2$ is not hydrogen;

$R_4$ is Z-T-W wherein Z represents —O—, —NH— or a single bond; T represents a straight- or branched-chain loweralkylene group; when Z is a single bond, T also represents an ethenylene or a propenylene group wherein the unsaturated carbon is at the single bond; when Z is —O—, T also represents an allylene group wherein the saturated carbon is at the oxygen; and W represents hydrogen, when T is allylene and Z is —O—, and Ar, wherein Ar is selected from thienyl, pyridinyl, furanyl, phenyl and substituted phenyl wherein there are one or more substituents on the phenyl independently selected from halogen or lower alkyl; and $R_5$ is hydrogen, halogen or lower alkyl;

or a derivative or physiologically acceptable salt, solvate or bioprecursor, or stereoisomer or enantiomer thereof;

formulated into a topically applicable, cosmetically or dermatologically acceptable vehicle, carrier or diluent therefor.

As employed throughout this specification, the term "halogen" means fluoro, chloro, bromo and iodo, with chloro and fluoro being preferred. The term "lower" as it modifies such radicals as alkyl means straight- or branched-chain radicals having up to six carbon atoms, e.g., methyl, ethyl, propyl, butyl, t-butyl, isopropyl, neopentyl, dimethylbutyl and the like. Methyl is the preferred lower alkyl.

"Pyridinyl" means the 2-, 3- and 4-isomers and their halogen- and lower alkyl-substituted analogs; "thienyl" means the 2- and 3-isomers and their halogen- and lower alkyl-substituted analogs; "furanyl" means the 2- and 3-isomers and their halogen- and lower alkyl-substituted analogs;

When "Ar" is phenyl, the substituents can be in the meta, ortho and/or para positions of the phenyl. The preferred substituents are halogen.

The $R_5$ substituents can be on one or more of the 5-, 6-, 7- or 8-positions of the imidazo[1,2-a]pyridine nucleus not already substituted by an $R_4$ substituent.

"Pharmaceutically acceptable salts" means salts wherein an acidic hydrogen forms an acid addition salt with an amine, e.g., the phosphate salt of 3-amino-2-methyl-8-phenylmethoxyimidazo-[1,2-a]pyridine. Suitable acids for the pharmaceutically acceptable acid addition salts include hydrochloric, sulfuric, phosphoric, nitric, acetic, propionic, maleic, ascorbic, citric and the like. The salts are prepared by procedures well known in the art.

A preferred subgroup of compounds of formula II are those wherein $R_2$ represents methyl or ethyl; $R_3$ represents —$NH_2$, —$NHC_2H_5$, —$CH_2CN$, —$CH_3$, —$CH_2OH$ or —$CH_2N$=C; R4 represents —$OCH_2Ar$, —$NHCH_2Ar$, —CH=CH—$(CH_2)_n$ Ar or —$CH_2CH_2(CH_2)_n$Ar wherein n is zero or one and Ar is as defined hereinabove; and $R_5$ is hydrogen, fluoro, chloro or methyl.

A further preferred subgroup are those compounds in which $R_4$ is at the 8-position and $R_5$, when other than hydrogen, is at the 7-position.

A still further preferred subgroup are those compounds in which $R_4$ is at the 8-position and is selected from phenylmethoxy, phenylethyl, 3-phenyl-1-propenyl, phenylethenyl, benzylamino, 3-thienylmethoxy and 3-thienylmethansmino; $R_2$ is methyl; $R_3$ is amino, cyanomethyl or methyl; and $R_5$ is hydrogen or methyl at the 7-position.

Non-limiting examples of imidazo[1,2-a]pyridine compounds within the scope of this invention are:

1. 3-amino-2-methyl-8-(2-phenylethyl)imidazo-[1,2-a]pyridine;
2. 2,3-dimethyl-8-[(2-phenyl)ethenyl]imidazo[1,2-a]pyridine;
3. 3-cyanomethyl-2-methyl-8-(3-phenyl-1-propenyl)imidazo[1,2-a]pyridine;
4. 2,7-dimethyl-8-phenylmethoxyimidazo[1,2-a]pyridine-3-acetonitrile;
5. 3-ethylamino-2-methyl-8-phenylmethoxyimidazo[1,2-a]pyridine;
6. 3-ethylamino-2-methyl-8-(2-phenylethyl)-imidazo[1,2-a]pyridine;
7. 3-amino-2-methyl-8-phenylmethoxyimidazo[1,2-a]pyridine;
8. 3-amino-2-ethyl-8-phenylmethoxyimidazo[1,2-a]pyridine;
9. 3-amino-2,6-dimethyl-8-phenylmethoxyimidazo[1,2-a]pyridine;
10. 3-amino-2,7-dimethyl-8-phenylmethoxyimidazo[1,2-a]pyridine;
11. 3-amino-8-(2-fluorophenylmethoxy)-2-methylimidazo[1,2-a]pyridine;
12. 3-amino-8-(4-chlorophenylmethoxy)-2-methylimidazo[1,2-a]pyridine;
13. 3-amino-2-methyl-8-[(3-thienylethyl)amino]imidazo[1,2-a]pyridine;
14. 3-amino-2-methyl-8-(3-thienylmethoxy)imidazo[1,2-a]pyridine;
15. 3-amino-2-methyl-8-(2-thienylmethoxy)imidazo[1,2-a]pyridine;
16. 2-methyl-3-isocyanomethyl-8-phenylmethoxyimidazo[1,2-a]pyridine;
17. 2-methyl-8-[3-thienylmethylamino]-imidazo[1,2-a]pyridine-3-acetonitrile;
18. 2-methyl-6-(2-phenylethyl)-imidazo[1,2-a]pyridine-3-acetonitrile;
19. 3-amino-2-methyl-6-(2-phenylethyl)-imidazo[1,2-a]pyridine;
20. 3-amino-8-(4-fluorophenylmethoxy)-2-methylimidazo[1,2-a]pyridine;
21. 2-methyl-8-(2,4,6-trimethylphenylmethoxy)imidazo[1,2-a]pyridine;

22. 8-(3,4-dichlorophenylmethoxy)-2-methylimidazo[1,2-a]pyridine;
23. 8-(2-fluorophenylmethoxy)-2-methylimidazo[1,2-a]pyridine-3-acetonitrile;
24. 8-(4-fluorophenylmethoxy)-2-methylimidazo[1,2-a]pyridine;
25. 2-methyl-8-(2-phenylethyl)imidazo[1,2-a]pyridine;
26. 8-(4-chlorophenylmethoxy)-2-methylimidazo[1,2-a]pyridine;
27. 2-methyl-8-(2-thienylmethoxy)imidazo[1,2-a]pyridine-3-acetonitrile;
28. 2-methyl-8-(2-pyridylmethoxy)imidazo[1,2-a]pyridine-3-acetonitrile;
29. 8-(3,4-dichlorophenylmethoxy)-2-methylimidazo[1,2-a]pyridine-3-acetonitrile;
30. 8-(4-methoxyphenylmethoxy)-2-methylimidazo[1,2-a]pyridine-3-acetonitrile;
31. 8-(4-t-butylphenylmethoxy-2-methylimidazo[1,2-a]pyridine-3-acetonitrile;
32. 8-(4-chlorophenylmethoxy)-methylimidazo[1,2-a]pyridine-3-acetonitrile;
33. 8-(3,4-dichlorophenylmethoxy)-3-hydroxymethyl-2-methylimidazo[1,2-a]pyridine;
34. 8-(4-chlorophenylmethoxy)-3-hydroxymethyl-2-methylimidazo[1,2-a]pyridine;
35. 8-phenylmethoxy-2-ethylimidazo[1,2-a]pyridine;
36. 8-phenylmethoxyimidazo[1,2-a]pyridine-3-acetonitrile;
37. 8-phenylmethoxy-2-hydroxymethylimidazo[1,2-a]pyridine;
38. 3-hydroxymethyl-2-methyl-8-(2-phenylethoxy)imidazo[1,2-a]pyridine;
39. 8-phenylmethoxy-2,3-dimethylimidazo[1,2-a]pyridine;
40. 2-methyl-8-(2-phenylethoxy)imidazo[1,2-a]pyridine-3-acetonitrile;
41. 2-methyl-8-(1-phenylethoxy)imidazo[1,2-a]pyridine-3-acetonitrile;
42. 2-methyl-8-(2-phenylethyl)imidazo[1,2-a]pyridine-3-acetonitrile;
43. 3-hydroxymethyl-2-methyl-8-(2-phenylethyl)imidazo[1,2-a]pyridine;
44. 2-methyl-8-(3-phenylpropoxyl)imidazo[1,2-a]pyridine-3-acetonitrile;
45. 8-phenylmethoxy-2-isopropylimidazo[1,2-a]pyridine-3-acetonitrile;
46. 8-phenylmethoxy-2-ethylimidazo[1,2-a]pyridine-3-acetonitrile;
47. 8-benzylamino-2,3-dimethylimidazo[1,2-a]pyridine;
48. 8-phenylmethoxy-2-methylimidazo[1,2-a]pyridine-3-acetonitrile;
49. 8-phenylmethoxy-3-hydroxymethyl-2-methylimidazo[1,2-a]pyridine;
50. 3-hydroxymethyl-8-(2-fluorophenylmethoxy)-2-methylimidazo[1,2-a]pyridine;
51. 8-(4-t-butylbenzyloxy)-3-hydroxymethyl-2-methylimidazo[1,2-a]pyridine;
52. 8-(2-fluorophenylmethoxy)-2-methylimidazo[1,2-a]pyridine-3-acetonitrile;
53. 8-(4-fluorophenylmethoxy)-2-methylimidazo[1,2-a]pyridine-3-acetonitrile;
54. 2-methyl-8-(2,4,6-trimethylphenylmethoxy)imidazo[1,2-a]pyridine-2-acetonitrile;
55. 8-benzylamino-2-methylimidazo[1,2-a]pyridine-3-acetonitrile;
56. 2-methyl-8-(3-thienylmethoxy)imidazo[1,2-a]pyridine-3-acetonitrile;
57. 2-methyl-8-phenylmethoxyimidazo[1,2-a]pyridine;
58. 8-allyloxy-2-methylimidazo[1,2-a]pyridine-3-acetonitrile;
59. 2-ethyl-8-phenylmethoxyimidazo[1,2-a]pyridine-3-acetonitrile;
60. 2-ethyl-3-methyl-8-phenylmethoxyimidazo[1,2-a]pyridine;
61. 3-amino-2-methyl-8-phenylmethoxyimidazo[1,2-a]pyridine and the phosphate acid addition salt thereof;
62. 2-methyl-8-(3-phenylpropyl)imidazo[1,2-a]pyridine-3-acetonitrile;
63. 2-methyl-6-benzylaminoimidazo[1,2-a]pyridine-3-acetonitrile;
64. 2-methyl-6-phenylmethoxyimidazo[1,2-a]pyridine-3-acetonitrile;
65. 2-methyl-5-benzylaminoimidazo[1,2-a]pyridine-3-acetonitrile;
66. 2-methyl-5-phenylmethoxyimidazo[1,2-a]pyridine-3-acetonitrile;
67. 2,3-dimethyl-5-phenylmethoxyimidazo[1,2-a]pyridine;
68. 2-methyl-7-phenylmethoxyimidazo[1,2-a]pyridine-3-acetonitrile;
69. 3-(cyanomethyl)-2-methyl-8-phenylmethoxy-imidazo[1,2-a]pyridine;
70. 3-amino-2-methyl-8-phenylmethoxyimidazo[1,2-a]pyrazine.

Preferred examples include 3-(cyanomethyl)-2-methyl-8-phenylmethoxy-imidazo[1,2-a]pyridine (SCH 28080) and 3-amino-2-methyl-8-phenylmethoxyimidazo[1,2-a]pyrazine (SCH 32651).

It is apparent that the compounds of this invention may be named in different ways. Thus, "benzyloxy" and "phenylmethoxy" are synonymous as are "cyanomethyl" and "acetonitrile". Therefore, as used herein, the names are interchangeable.

In a further aspect, the present invention concerns a method for lightening/depigmenting the skin comprising applying to the skin in need thereof a composition comprising a skin-lightening/depigmenting effective amount of at least one compound or derivative thereof which is an inhibitor of Type I H+, K+-ATPases.

In a preferred embodiment of this aspect of the present invention, the method for lightening/depigmenting the skin comprises applying to the skin in need thereof a composition comprising a skin-lightening/depigmenting effective amount of at least one compound or derivative thereof represented by the structural formula:

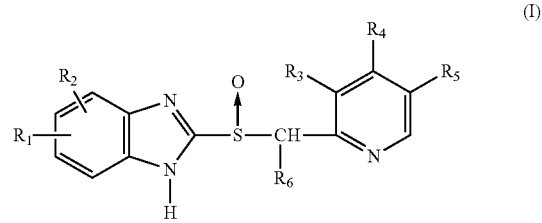

(I)

wherein:
$R_1$ and $R_2$ are same or different and are each selected from the group consisting of hydrogen, alkyl, carbomethoxy, carboethoxy, alkoxy, and alkanoyl, any of which may be halogen-substituted, and halogen;
$R_6$ is selected from the group consisting of hydrogen, methyl, and ethyl; and
$R_3$, $R_4$ and $R_5$ are the same or different and are each selected from the group consisting of hydrogen, methyl, methoxy, ethoxy, methoxyethoxy, ethoxyethoxy, propoxy, propoxymethoxy, and the like, any of which may be halogen-substituted;

or a derivative or physiologically acceptable salt, solvate or bioprecursor, or stereoisomer or enantiomer thereof;

formulated into a topically applicable, cosmetically or dermatologically acceptable vehicle, carrier or diluent therefor.

Alkyl $R_1$ and $R_2$ of formula I are suitably alkyl having up to 7 carbon atoms, preferably up to 4 carbon atoms. Thus, alkyl R may be methyl, ethyl, n-propyl, isopropyl, n-butyl or isobutyl, whether or not halogen-substituted.

Halogen $R_1$ and $R_2$ are chloro, bromo, fluoro, or iodo.

Alkoxy $R_1$ and $R_2$ are suitably alkoxy groups having up to 5 carbon atoms, preferably up to 3 carbon atoms, such as methoxy, ethoxy, n-propoxy, or isopropoxy, including halogen-substituted groups.

Alkanoyl $R_1$ and $R_2$ have preferably up to 4 carbon atoms and are e.g. formyl, acetyl, or propionyl, preferably acetyl, including halogen-substituted groups.

One preferred group of compounds of the general formula I for use in this method of the present invention are those wherein $R_1$ and $R_2$ are the same or different and are each selected from the group consisting of hydrogen, alkyl, and alkoxy, whether or not halogen-substituted, $R_6$ is selected from the group consisting of hydrogen, methyl and ethyl, and $R_3$, $R_4$, and $R_5$ are the same or different and are each selected from the group consisting of hydrogen, alkyl and alkoxy, whether or not substituted by halogen.

A second preferred group of compounds of the general formula I are those wherein $R_1$ and $R_2$ are the same or different and are each selected from the group consisting of hydrogen, methyl, methyl substituted by halogen, methoxy, and methoxy substituted by halogen, $R_6$ is hydrogen, $R_3$, $R_4$, and $R_5$ are the same or different and are each selected from the group consisting of hydrogen, methyl, ethyl, propyl, methoxy, ethoxy, propoxy, methoxymethoxy, ethoxyethoxy, propoxypropoxy, methoxyethoxy, ethoxymethoxy, methoxypropoxy, propoxymethoxy, ethoxypropoxy, propoxyethoxy, whether or not substituted by halogen.

Non-limiting examples of preferred compounds are those in which R1 and R2 are each hydrogen or methoxy, R3 and R5 are methyl and R4 is methoxy; in which $R_1$, $R_2$, $R_5$ and $R_6$ are hydrogen, $R_3$ is methyl and $R_4$ is propoxymethoxy; in which $R_1$, $R_2$, $R_3$, $R_1$, $R_5$ and $R_6$ all are hydrogen; in which $R_1$, $R_2$, $R_5$ and $R_6$ all are hydrogen, $R_3$ is methyl and $R_4$ is ethoxy substituted by halogen; and in which $R_1$ and $R_2$ are hydrogen or methoxy substituted by halogen, $R_6$ is hydrogen, $R_3$ is hydrogen and $R_1$ and $R_5$ are methoxy.

Most preferred for use in the methods of the present invention are omeprazole, its derivatives and analogues.

In a further preferred embodiment of this aspect of the present invention, the method for lightening/depigmenting the skin comprises applying to the skin in need thereof a composition comprising a skin lightening/depigmenting effective amount of at least one compound or derivative thereof represented by the structural formula:

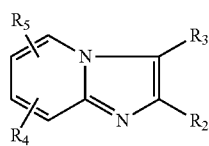

(II)

wherein:
$R_2$ is hydrogen, lower alkyl or hydroxy lower alkyl;
$R_3$ is lower alkyl, —CH$_2$CN, hydroxy lower alkyl, —NO, —CH$_2$N═C or

(wherein $R_6$ and $R_7$ are independently selected from the group consisting of hydrogen and lower alkyl) or hydrogen provided $R_2$ is not hydrogen; R4 is Z-T-W wherein Z represents —O—, —NH— or a single bond; T represents a straight- or branched-chain lower-alkylene group; when Z is a single bond, T also represents an ethenylene or a propenylene group wherein the unsaturated carbon is at the single bond; when Z is —O—, T also represents an allylene group wherein the saturated carbon is at the oxygen; and W represents hydrogen, when T is allylene and Z is —O—, and Ar, wherein Ar is selected from thienyl, pyridinyl, furanyl, phenyl and substituted phenyl wherein there are one or more substituents on the phenyl independently selected from halogen or lower alkyl; and $R_5$ is hydrogen, halogen or lower alkyl;

or a derivative or physiologically acceptable salt, solvate or bioprecursor, or stereoisomer or enantiomer thereof;

formulated into a topically applicable, cosmetically or dermatologically acceptable vehicle, carrier or diluent therefor.

A preferred subgroup of compounds of Formula II for use in this method are those wherein $R_2$ represents methyl or ethyl; $R_3$ represents —NH$_2$, —NHC$_2$H3, —CH$_2$CN, —CH$_3$, —CH$_2$OH or —CH$_2$N═C; R4 represents —OCH$_2$Ar, —NHCH$_2$Ar, —CH═CH—(CH$_2$)$_n$ Ar or —CH$_2$CH$_2$ (CH$_2$)$_n$Ar wherein n is zero or one and Ar is as defined hereinabove; and $R_5$ is hydrogen, fluoro, chloro or methyl.

A further preferred subgroup of compounds in wherein $R_4$ is at the 8-position and $R_5$, when other than hydrogen, is at the 7-position.

A still further preferred subgroup are those compounds in which $R_4$ is at the 8-position and is selected from phenylmethoxy, phenylethyl, 3-phenyl-1-propenyl, phenylethenyl, benzylamino, 3-thienylmethoxy and 3-thienylmethanamino; $R_2$ is methyl; $R_3$ is amino, cyanomethyl or methyl; and $R_5$ is hydrogen or methyl at the 7-position.

Non-limiting examples of imidazo[1,2-a]pyridine compounds within the scope of this invention are:
1. 3-amino-2-methyl-8-(2-phenylethyl)imidazo-[1,2-a]pyridine;
2. 2,3-dimethyl-8-[(2-phenyl)ethenyl]imidazo[1,2-a]pyridine;
3. 3-cyanomethyl-2-methyl-8-(3-phenyl-1-propenyl)imidazo[1,2-a]pyridine;
4. 2,7-dimethyl-8-phenylmethoxyimidazo[1,2-a]pyridine-3-acetonitrile;
5. 3-ethylamino-2-methyl-8-phenylmethoxyimidazo[1,2-a]pyridine;
6. 3-ethylamino-2-methyl-8-(2-phenylethyl)-imidazo[1,2-a]pyridine;
7. 3-amino-2-methyl-8-phenylmethoxyimidazo[1,2-a]pyridine;
8. 3-amino-2-ethyl-8-phenylmethoxyimidazo[1,2-a]pyridine;
9. 3-amino-2,6-dimethyl-8-phenylmethoxyimidazo[1,2-a] pyridine;
10. 3-amino-2,7-dimethyl-8-phenylmethoxyimidazo[1,2-a] pyridine;

11. 3-amino-8-(2-fluorophenylmethoxy)-2-methylimidazo[1,2-a]pyridine;
12. 3-amino-8-(4-chlorophenylmethoxy)-2-methylimidazo[1,2-a]pyridine;
13. 3-amino-2-methyl-8-[(3-thienylethyl)amino]imidazo[1,2-a]pyridine;
14. 3-amino-2-methyl-8-(3-thienylmethoxy)imidazo[1,2-a]pyridine;
15. 3-amino-2-methyl-8-(2-thienylmethoxy)imidazo[1,2-a]pyridine;
16. 2-methyl-3-isocyanomethyl-8-phenylmethoxyimidazo[1,2-a]pyridine;
17. 2-methyl-8-[3-thienylmethylamino]-imidazo[1,2-a]pyridine-3-acetonitrile;
18. 2-methyl-6-(2-phenylethyl)-imidazo[1,2-a]pyridine-3-acetonitrile;
19. 3-amino-2-methyl-6-(2-phenylethyl)-imidazo[1,2-a]pyridine;
20. 3-amino-8-(4-fluorophenylmethoxy)-2-methylimidazo[1,2-a]pyridine;
21. 2-methyl-8-(2,4,6-trimethylphenylmethoxy)imidazo[1,2-a]pyridine;
22. 8-(3,4-dichlorophenylmethoxy)-2-methylimidazo[1,2-a]pyridine;
23. 8-(2-fluorophenylmethoxy)-2-methylimidazo[1,2-a]pyridine-3-acetonitrile;
24. 8-(4-fluorophenylmethoxy)-2-methylimidazo[1,2-a]pyridine;
25. 2-methyl-8-(2-phenylethyl)imidazo[1,2-a]pyridine;
26. 8-(4-chlorophenylmethoxy)-2-methylimidazo[1,2-a]pyridine;
27. 2-methyl-8-(2-thienylmethoxy)imidazo[1,2-a]pyridine-3-acetonitrile;
28. 2-methyl-8-(2-pyridylmethoxy)imidazo[1,2-a]pyridine-3-acetonitrile;
29. 8-(3,4-dichlorophenylmethoxy)-2-methylimidazo[1,2-a]pyridine-3-acetonitrile;
30. 8-(4-methoxyphenylmethoxy)-2-methylimidazo[1,2-a]pyridine-3-acetonitrile;
31. 8-(4-t-butylphenylmethoxy-2-methylimidazo[1,2-a]pyridine-3-acetonitrile;
32. 8-(4-chlorophenylmethoxy)-methylimidazo[1,2-a]pyridine-3-acetonitrile;
33. 8-(3,4-dichlorophenylmethoxy)-3-hydroxymethyl-2-methylimidazo[1,2-a]pyridine;
34. 8-(4-chlorophenylmethoxy)-3-hydroxymethyl-2-methylimidazo[1,2-a]pyridine;
35. 8-phenylmethoxy-2-ethylimidazo[1,2-a]pyridine;
36. 8-phenylmethoxyimidazo[1,2-a]pyridine-3-acetonitrile;
37. 8-phenylmethoxy-2-hydroxymethylimidazo[1,2-a]pyridine;
38. 3-hydroxymethyl-2-methyl-8-(2-phenylethoxy)imidazo[1,2-a]pyridine;
39. 8-phenylmethoxy-2,3-dimethylimidazo[1,2-a]pyridine;
40. 2-methyl-8-(2-phenylethoxy)imidazo[1,2-a]pyridine-3-acetonitrile;
41. 2-methyl-8-(1-phenylethoxy)imidazo[1,2-a]pyridine-3-acetonitrile;
42. 2-methyl-8-(2-phenylethyl)imidazo[1,2-a]pyridine-3-acetonitrile;
43. 3-hydroxymethyl-2-methyl-8-(2-phenylethyl)imidazo[1,2-a]pyridine;
44. 2-methyl-8-(3-phenylpropoxyl)imidazo[1,2-a]pyridine-3-acetonitrile;
45. 8-phenylmethoxy-2-isopropylimidazo[1,2-a]pyridine-3-acetonitrile;
46. 8-phenylmethoxy-2-ethylimidazo[1,2-a]pyridine-3-acetonitrile;
47. 8-benzylamino-2,3-dimethylimidazo[1,2-a]pyridine;
48. 8-phenylmethoxy-2-methylimidazo[1,2-a]pyridine-3-acetonitrile;
49. 8-phenylmethoxy-3-hydroxymethyl-2-methylimidazo[1,2-a]pyridine;
50. 3-hydroxymethyl-8-(2-fluorophenylmethoxy)-2-methylimidazo[1,2-a]pyridine;
51. 8-(4-t-butylbenzyloxy)-3-hydroxymethyl-2-methylimidazo[1,2-a]pyridine;
52. 8-(2-fluorophenylmethoxy)-2-methylimidazo[1,2-a]pyridine-3-acetonitrile;
53. 8-(4-fluorophenylmethoxy)-2-methylimidazo[1,2-a]pyridine-3-acetonitrile;
54. 2-methyl-8-(2,4,6-trimethylphenylmethoxy)imidazo[1,2-a]pyridine-2-acetonitrile;
55. 8-benzylamino-2-methylimidazo[1,2-a]pyridine-3-acetonitrile;
56. 2-methyl-8-(3-thienylmethoxy)imidazo[1,2-a]pyridine-3-acetonitrile;
57. 2-methyl-8-phenylmethoxyimidazo[1,2-a]pyridine;
58. 8-allyloxy-2-methylimidazo[1,2-a]pyridine-3-acetonitrile;
59. 2-ethyl-8-phenylmethoxyimidazo[1,2-a]pyridine-3-acetonitrile;
60. 2-ethyl-3-methyl-8-phenylmethoxyimidazo[1,2-a]pyridine;
61. 3-amino-2-methyl-8-phenylmethoxyimidazo[1,2-a]pyridine and the phosphate acid addition salt thereof;
62. 2-methyl-8-(3-phenylpropyl)imidazo[1,2-a]pyridine-3-acetonitrile;
63. 2-methyl-6-benzylaminoimidazo[1,2-a]pyridine-3-acetonitrile;
64. 2-methyl-6-phenylmethoxyimidazo[1,2-a]pyridine-3-acetonitrile;
65. 2-methyl-5-benzylaminoimidazo[1,2-a]pyridine-3-acetonitrile;
66. 2-methyl-5-phenylmethoxyimidazo[1,2-a]pyridine-3-acetonitrile;
67. 2,3-dimethyl-5-phenylmethoxyimidazo[1,2-a]pyridine;
68. 2-methyl-7-phenylmethoxyimidazo[1,2-a]pyridine-3-acetonitrile;
69. 3-(cyanomethyl)-2-methyl-8-phenylmethoxy-imidazo[1,2-a]pyridine;
70. 3-amino-2-methyl-8-phenylmethoxyimidazo[1,2-a]pyrazine.

Preferred examples of compounds useful in this method of the present invention include 3-(cyanomethyl)-2-methyl-8-phenylmethoxy-imidazo[1,2-a]pyridine (SCH 28080) and 3-amino-2-methyl-8-phenylmethoxyimidazo[1,2-a]pyrazine (SCH 32651).

A further aspect of the present invention concerns a method of screening compounds for efficacy in modulating melanin synthesis. In one embodiment of this aspect of the invention, the compounds are screened for efficacy in decreasing the amount of melanin in cells, the method comprising (a) selecting a compound to be tested; (b) incubating melanocytes or melanoma cells with the test compound at various concentrations and with a positive control compound; and (c) determining melanin content. In a further embodiment of this aspect of the invention, the compounds are screened for efficacy in lowering the pH of cells, the method comprising (a) selecting a compound to be tested; (b) incubating melanocytes or melanoma cells with the test compound at various concentrations and with a positive control compound; (c) incubating the melanocytes or melanoma cells with a weak base, such as 30

μM DAMP; (d) incubating the cells with a labelled antibody to the weak base, such as fluorescent FITC-labeled rabbit anti-DNP antibody; and (e) assessing the change in pH, such as by observing the amount of fluorescence produced.

The inhibitors of Type I $H^+$, $K^+$-ATPases may be used in a pharmaceutical product or a cosmetic or dermatological product. Skin compositions of the invention may comprise from about 0.00005% to about 0.5% of the active compound by weight of the total composition, more preferably from about 0.0005% to about 0.05%, more preferably still from about 0.005% to about 0.01%, such as about 0.0035%.

Cosmetic or dermatological compositions of the present inventions my be found in a variety of forms, such as anhydrous compositions, aqueous-based solutions, serums, gels, a suspension, a dispersion, aerosol, milk creams, lotions, mousses, sticks, sprays, ointments, essences, pastes, microcapsules, or color cosmetic compositions such as foundation, blush, eyeshadow, and the like. They may contain many other additional cosmetically and/or dermatologically acceptable ingredients, such as additional skin lightening agents or tyrosinase inhibitors, antioxidants, anti-inflammatory agents, botanicals, humectants, moisturizers, sunscreens, preservatives, colorants, perfumes, and the like. In the case where the composition is in the anhydrous form the Type I H+, K+-ATPase inhibitor compound or derivative thereof may be solubilized or dispersed in the oil phase of the emulsion; or if the Type I $H^+$, $K^+$-ATPase inhibitor compound or derivative thereof is water soluble it may be solvated in polar solvents, typically ingredients referred to as humectants such as glycerine or alkylene glycols prior to formation of an anhydrous emulsion. If the composition is in the emulsion form, the Type I $H^+$, $K^+$-ATPase inhibitor compound or derivative thereof may be found in the water phase or the oil phase of the emulsion depending on the type of derivative. For example, certain hydrophilic derivatives which are water soluble will generally be solubilized in the water phase of the emulsion. Certain other derivatives which are lipophilic in nature will more likely be found in the oil phase of the emulsion.

Suitable serums or gels will generally comprise from about 1-99% water, and optionally from about 0.001-30% of an aqueous phase thickening agent. The other ingredients mentioned herein may be present in the percentage ranges set forth.

Typical skin creams or lotions comprise from about 5-98% water, 1-85% oil, and from about 0.1 to 20% of one or more surfactants. Preferably the surfactants are nonionic and may be in the form of silicones or organic nonionic surfactants.

Typical color cosmetic compositions such as foundations, blush, eyeshadow, and the like, will preferably contain from about 5-98% water, 1-85% oil, and from about 0.1 to 20% of one or more surfactants in addition to from about 0.1 to 65% of particulates that are pigments or a combination of pigments and powders.

In the case where the compositions are in the form of aqueous solutions, dispersions or emulsions, in addition to water the aqueous phase may contain one or more aqueous phase structuring agents, that is, an agent that increases the viscosity or thickens, the aqueous phase of the composition. This is particularly desirable when the composition is in the form of a serum or gel. The aqueous phase structuring agent should be compatible with the Type I $H^+$, $K^+$-ATPase inhibitor compound or derivative thereof, particularly if the particular Type I $H^+$, $K^+$-ATPase inhibitor compound or derivative thereof is water soluble, and also compatible with the other ingredients in the formulation. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below. When the Type I $H^+$, $K^+$-ATPase inhibitor compound or derivative thereof is in the water soluble form, the aqueous phase thickening agent also contributes to stabilizing this ingredient in the composition and improving penetration into the stratum corneum. Such structuring agents may include the following:

A. Polysaccharides

Polysaccharides may be suitable aqueous phase thickening agents. Examples of such polysaccharides include naturally derived materials such as agar, agarose, alicaligenes polysaccharides, algin, alginic acid, *acacia* gum, amylopectin, chitin, dextran, *cassia* gum, cellulose gum, gelatin, gellan gum, hyaluronic acid, hydroxyethyl cellulose, methyl cellulose, ethyl cellulose, pectin, *sclerotium* gum, xanthan gum, pectin, trehelose, gelatin, and so on.

B. Acrylate Polymers

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alkyl methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

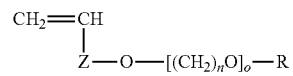

wherein Z is $—(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of the formula:

in which R' denotes H or CH$_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly) ethylene glycol dimethacrylate and methylenebisacrylamide. Commercial examples of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/C$_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One particularly suitable type of aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer as found in AVC dispersed in a mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

C. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CTFA names polyglycerin-20, polyglycerin-40, and the like.

In the event the compositions of the invention are in anhydrous or emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure or a vapor pressure of at least about 2 mm. of mercury at 20° C. The term "nonvolatile" means that the oil has a vapor pressure of less than about 2 mm. of mercury at 20° C. Suitable oils may include the following:

A. Volatile Oils

Suitable volatile oils generally have a viscosity ranging from about 0.5 to 5 centistokes 25° C. and include linear silicones, cyclic silicones, paraffinic hydrocarbons, or mixtures thereof. Volatile oils may be used to promote more rapid drying of the skin care composition after it is applied to skin. Volatile oils are more desirable when the skin care products containing the Type I H$^+$, K$^+$-ATPase inhibitor compound or derivative thereof are being formulated for consumers that have combination or oily skin. The term "combination" with respect to skin type means skin that is oily in some places on the face (such as the T-zone) and normal in others.

1. Volatile Silicones

Cyclic silicones are one type of volatile silicone that may be used in the composition. Such silicones have the general formula:

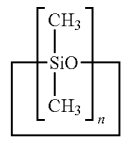

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

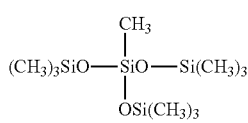

Methyl trimethicone may be purchased from Shin-Etsu Silicones under the tradename TMF-1.5, having a viscosity of 1.5 centistokes at 25° C.

2. Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available under the ISO-PARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

B. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

1. Esters

Suitable esters are mono-, di-, and triesters. The composition may comprise one or more esters selected from the group, or mixtures thereof.

(a) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

(b). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(c). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

2. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

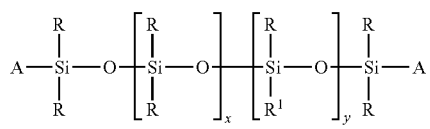

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

5. Fluorinated Oils

Various types of fluorinated oils may also be suitable for use in the compositions including but not limited to fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588, all of which are hereby incorporated by reference, which are commercially available from Montefluos under the trademark Fomblin.

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The oil phase structuring agent is compatible with the Type I $H^+$, $K^+$-ATPase inhibitor compound or derivative thereof, particularly if the Type I $H^+$, $K^+$-ATPase inhibitor compound or derivative thereof is soluble in the nonpolar oils forming the oil phase of the composition. The term "compatible" means that the oil phase structuring agent and Type I $H^+$, $K^+$-ATPase inhibitor compound or derivative thereof are capable of being formulated into a cosmetic product that is generally stable. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both. Such oil structuring agents may include the following:

A. Silicone Structuring Agents

A variety of oil phase structuring agents may be silicone based, such as silicone elastomers, silicone gums, silicone waxes, and linear silicones having a degree of polymerization that provides the silicone with a degree of viscosity such that when incorporated into the cosmetic composition it is capable of increasing the viscosity of the oil phase. Examples of silicone structuring agents include, but are not limited to:

1. Silicone Elastomers

Silicone elastomers suitable for use in the compositions of the invention include those that are formed by addition reaction curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252; U.S. Pat. No. 5,760,116; U.S. Pat. No. 5,654,362; and Japanese Patent Application JP 61-18708; each of which is herein incorporated by reference in its entirety. It is particularly desirable to incorporate silicone elastomers into the compositions of the invention because they provide excellent "feel" to the composition, are very stable in cosmetic formulations, and relatively inexpensive.

2. Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula:

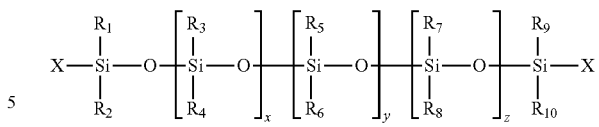

wherein $R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

3. Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

4. Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

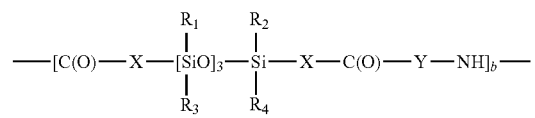

X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

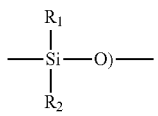

and Y is:
(a) a linear or branched alkylene having from about 1-40 carbon atoms which may be substituted with:
  (i) one or more amide groups having the general formula $R_1CONR_1$, or
  (ii) $C_{5-6}$ cyclic ring, or
  (iii) phenylene which may be substituted with one or more $C_{1-10}$ alkyl groups, or
  (iv) hydroxy, or
  (v) $C_{3-8}$ cycloalkane, or
  (vi) $C_{1-20}$ alkyl which may be substituted with one or more hydroxy groups, or
  (vii) $C_{1-10}$ alkyl amines; or
(b) $TR_5R_6R_7$ wherein $R_5$, $R_6$, and $R_7$, are each independently a $C_{1-10}$ linear or branched alkylenes, and T is $CR_8$ wherein $R_5$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

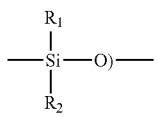

Preferred is where $R_1$, $R_2$, $R_3$, and $R_4$ are $C_{1-10}$, preferably methyl; and X and Y are a linear or branched alkylene. Preferred are silicone polyamides having the general formula:

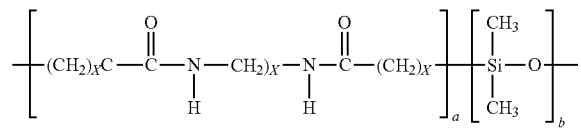

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

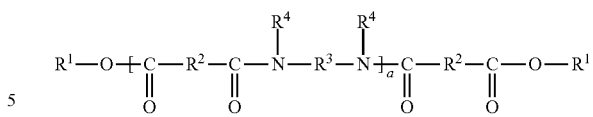

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a $C_{30-42}$ hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups R4 representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

5. Natural or Synthetic Organic Waxes

Also suitable as the oil phase structuring agent may be one or more natural or synthetic waxes such as animal, vegetable, or mineral waxes. Preferably such waxes will have a higher melting point such as from about 50 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

6. Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

7. Silicas and Silicates

Another type of structuring agent that may be used in the compositions are silicas, silicates, silica silylate, and alkali metal or alkaline earth metal derivatives thereof. These silicas and silicates are generally found in the particulate form and include silica, silica silylate, magnesium aluminum silicate, and the like.

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

A. Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

1. Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

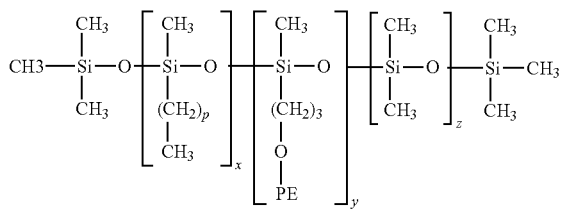

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

2. Crosslinked Silicone Surfactants

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986, U.S. Pat. No. 5,412,004, U.S. Pat. No. 5,837,793 and U.S. Pat. No. 5,811,487, the contents of which are hereby incorporated by reference in their entireties.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

B. Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene, glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are those formed by the reaction of a carboxylic acid with an alkylene oxide or with a polymeric ether. The resulting products have the general formula:

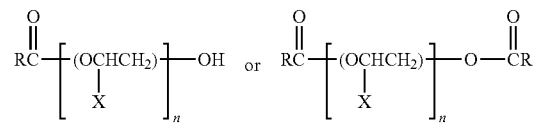

where RCO is the carboxylic ester radical, X is hydrogen or lower alkyl, and n is the number of polymerized alkoxy groups. In the case of the diesters, the two RCO-groups do not need to be identical. Preferably, R is a C6-30 straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula:

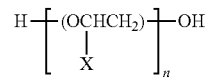

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

It may be desirable to include one or more penetration enhancers in the composition. Penetration enhancers are ingredients that enhance the penetration of the Type I $H^+$, $K^+$-ATPase inhibitor compound or derivative thereof into the keratinous surface to which the composition is applied. If present, suitable penetration enhancers may range from about 0.001 to 30%, preferably from about 0.005 to 25%, more preferably from about 0.01 to 20%. Suitable penetration enhancers include, but are not limited to lipophilic materials such as saturated or unsaturated $C_{6-40}$ straight or branched chain fatty acids, or saturated or unsaturated $C_{6-40}$ straight or branched chain fatty alcohols. Examples include oleic acid, linoleic acid, stearic acid, oleyl alcohol, linoleyl alcohol, and the like.

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{24}$ alkylene glycols, most particularly butylene glycol.

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina pavonica* extract, *Thermus thermophilis* ferment extract, *Camelina sativa* seed oil, *Boswellia serrata* extract, olive extract, *Aribodopsis thaliana* extract, *Acacia dealbata* extract, *Acer saccharimum* (sugar maple), acidopholus, acorus, aesculus, agaricus, agave, agrimonia, *algae*, aloe, citrus, *brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pynrus malus, Saxifraga sarmentosa, Vitis vinifera, Morus nigra, Scutellaria baicalensis, Anthemis nobilis, Salvia sclarea, Rosmarinus officianalis, Citrus medica Limonum, Panax, Ginseng, Siegesbeckia orientalis, Fructus mume, Ascophyllum nodosum, Bifida* Ferment lysate, *Glycine soja* extract, *Beta vulgaris, Haberlea rhodopensis, Polygonum cuspidatum, Citrus Aurantium dulcis, Vitis vinifera, Selaginella tamariscina, Humulus lupulus, Citrus reticulata* Peel, *Punica granatum, Asparagopsis, Curcuma longa, Menyanthes trifoliata, Helianthus anmuus, Hordeum vulgare, Cucumis sativus, Evernia prunastri, Evernia furfuracea,* and mixtures thereof.

It may be desirable to include one or more tyrosinase inhibiting agents in the compositions of the invention. Such tyrosinase inhibitors may include kojic acid, arbutin and hydroquinone.

It may be desirable to include one or more additional skin-lightening compounds in the compositions of the present invention. Suitable skin-lightening compounds include ascorbic acid and its derivatives, e.g., magnesium ascorbyl phosphate, ascorbyl glucosamine, ascorbyl palmitate. Other skin-lightening agents include adapalene, aloe extract, ammonium lactate, anethole derivatives, apple extract, azelaic acid, bamboo extract, bearberry extract, bletilla tuber, *Bupleurum falcatum* extract, burnet extract, butyl hydroxy anisole, butyl hydroxy toluene, deoxyarbutin, 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, ellagic acid, escinol, estragole derivatives, FADE OUT (available from Pentapharm), Fangfeng, fennel extract, *ganoderma* extract, gaoben, GATULINE WHITENING (available from Gattlefosse), genistic acid and its derivatives, glabridin and its derivatives, gluco pyranosyl-1-ascorbate, gluconic acid, glycolic acid, green tea extract, placenta extract, 4-Hydroxy-5-methyl-3[2H]-furanone, 4 hydroxyanisole and its derivatives, 4-hydroxy benzoic acid derivatives, hydroxycaprylic acid, inositol ascorbate, lactic acid, lemon extract, linoleic acid, MELA WHITE (available from Pentapharm), *Morus alba* extract, mulberry root extract, niacinamide, 5-octanoyl salicylic acid, parsley extract, *phellinus linteus* extract, pyrogallol derivatives, retinoic acid, retinol, retinyl esters (acetate, propionate, palmitate, linoleate), 2,4 resorcinol derivatives, 3,5 resorcinol derivatives, rose fruit extract, salicylic acid, 3,4,5 trihydroxybenzyl derivatives, tranexamic acid, vitamin D3 and its analogs, and mixtures thereof.

It may also be desirable to include one or more sunscreens in the compositions of the invention. Such sunscreens include chemical UVA or UVB sunscreens or physical sunscreens in the particulate form. Inclusion of sunscreens in the compositions containing the Type I $H^+$, $K^+$-ATPase inhibitor compound or derivative thereof will provide additional protection to skin during daylight hours and promote the effectiveness of the Type I $H^+$, $K^+$-ATPase inhibitor compound or derivative thereof on the skin. Such sunscreen compounds may include the following:

A. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

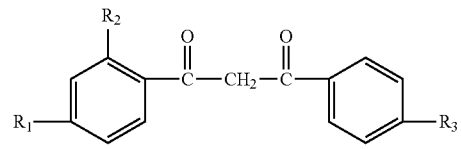

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

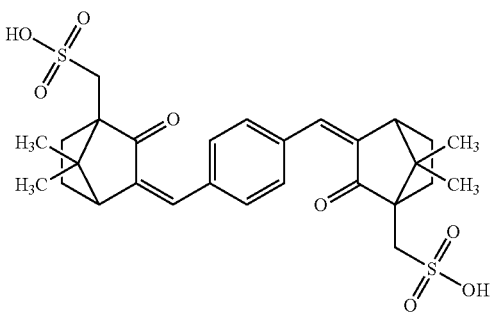 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

B. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

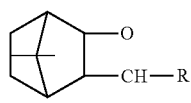

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

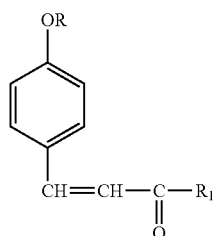

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

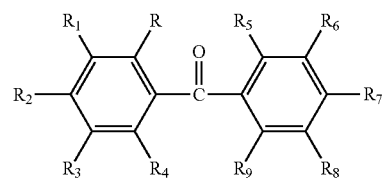

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

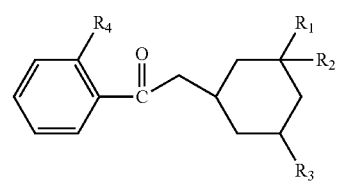

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

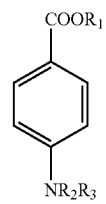

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula:

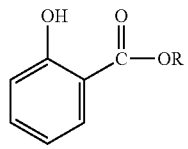

wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art.

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition. Suitable particulate materials may include the following:

A. Powders

The particulate matter may be colored or non-colored (for example white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

B. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, niacin, niacinamide, nicotinic acid, nicotinic acid dinucleotide, and so on, as well as coenzymes such as thiamine pyrophoshate, flavin adenine dinucleotide, folic acid, pyridoxal phosphate, tetrahydrofolic acid, and so on. Also Vitamin A and derivatives thereof are suitable. Examples are retinyl palmitate, retinol, retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

It may be desirable to include one or more film forming ingredients in the cosmetic compositions of the invention. Suitable film formers are ingredients that contribute to formation of a film on the keratinous surface. In some cases the film formers may provide films that provide long wearing or transfer resistant properties such that the cosmetic applied to the keratinous surface will remain for periods of time ranging from 3 to 16 hours. If present, such film formers may range from about 0.01 to 50%, preferably from about 0.1 to 40%, more preferably from about 0.5 to 35% by weight of the total composition. The film formers are most often found in the polymeric form and may be natural or synthetic polymers. If synthetic, silicone polymers, organic polymers or copolymers of silicones and organic groups may be acceptable. Suitable film formers include, but are not limited to:

A. Silicone Resins

One particularly suitable type of silicone film former is a silicone resin. Silicone resins are generally highly crosslinked structures comprising combinations of M, D, T, and Q units. The term "M" means a monofunctional siloxy unit having the general formula:

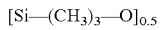
[Si—(CH$_3$)$_3$—O]$_{0.5}$

In cases where the M unit is other than methyl (such as ethyl, propyl, ethoxy, etc.) the M unit may have a prime after it, e.g. M'.

The term "D" means a difunctional siloxy unit having the general formula:

[Si—(CH$_3$)$_2$—O]$_{1.0}$

The difunctional unit may be substituted with alkyl groups other than methyl, such as ethyl, propyl, alkylene glycol, and the like, in which case the D unit may be referred to as D', with the prime indicating a substitution.

The term "T" means a trifunctional siloxy unit having the general formula:

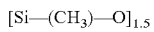
[Si—(CH$_3$)—O]$_{1.5}$

The trifunctional unit may be substituted with substituents other than methyl, in which case it may be referred to as T'.

The term "Q" refers to a quadrifunctional siloxy unit having the general formula:

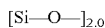
[Si—O—]$_{2.0}$

The silicone resins that may be used as film formers in the compositions of the invention preferably comprise highly crosslinked combinations of M, T, and Q units. Examples of such resins include trimethylsiloxysilicate which can be purchased from Dow Corning Corporation as 749 Fluid, or from GE Silicones under the SR-1000 tradename. Also suitable is a silicone resin that contains a large percentage of T groups, such as MK resin sold by Wacker-Chemie, having the CTFA name polymethylsilsesquioxane.

B. Copolymers of Silicone and Organic Monomers

Also suitable for use as the film formers are copolymers of silicone and organic monomers such as acrylates, methacrylates, and the like. Examples of such suitable film forming polymers include those commonly referred to as silicone acrylate or vinyl silicone copolymers, such as those sold by 3M under the brand name "Silicone Plus" polymers such as SA-70, having the CTFA name Polysilicone-7 and is a copolymer of isobutylmethacrylate and n-butyl endblocked polydimethylsiloxane propyl methacrylate; or VS-70 having the CTFA name Polysilicone-6, which is a copolymer of dimethylsiloxane and methyl-3 mercaptopropyl siloxane reacted with isobutyl methacrylate; or VS-80, having the CTFA name Polysilicone-8, which has the general structure:

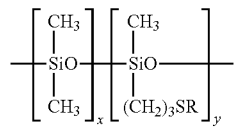

where R represents the acrylates copolymer radical.

C. Organic Polymers

Also suitable as film formers include various types of organic polymers such as polymers formed from acrylic acid, methacrylic acid, or their simple $C_{1-10}$ carboxylic acid esters, such as methyl methacrylate, methyl acrylate, and the like.

Also suitable are various types of natural polymers such as shellac, natural resins, chitin, and the like.

It may also be desirable to incorporate one or more DNA repair enzymes into the composition of the invention. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI Dermatics under the trade name Roxisomes®, and has the INCI name *Arabidopsis Thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing 06-methyl guanine base mutation damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of a species of *micrococcus*), lecithin, and water. Photosomes® comprises a mixture of plankton extract (which is the extract of a biomass which includes enzymes from one or more of the following organisms: thalassoplankton, green micro-*algae*, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

Other suitable DNA repair enzymes include Endonuclease V, which may be produced by the denV gene of the bacteriophage T4. Also suitable are T4 endonuclease; O-6-methylguanine-DNA methyltransferases; photolyases, base glycosylases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; polymerases; ligases; and topoisomerases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH);

8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as O-6-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch excision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma Pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2HS); CDK activating kinase (CDK7, CCNH); cyclin G1-interacting protein (MNAT1); DNA excision repair protein ERCC-1 or RAD-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog (REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

The invention is further illustrated by the following non-limiting examples.

EXAMPLES

Example I

Preparation of a Skin-Lightening Composition

TABLE II

| SKIN-LIGHTENING COMPOSITION | |
|---|---|
| MATERIAL | WEIGHT PERCENT |
| Phase I | |
| Water/phenyl trimethicone/dicapryl carbonate/ cimethicone/phospholipids | 51.0000 |
| Sodium dehydroacetate | 0.1000 |
| Disodium EDTA | 0.1400 |
| Phase II | |
| Glycerin | 3.0000 |
| Omeprazole | 0.0035 |
| Aluminum starch octenylsuccinate | 1.0000 |
| Phase III | |
| Purified water | 40.8065 |
| Acrylates/C10-30 alkyl acrylate crosspolymer | 0.3000 |
| Carbomer | 0.3500 |
| Phase IV | |
| Glycerin | 1.0000 |
| Xanthan gum | 0.2000 |
| Phase V | |
| Purified water | 2.0000 |
| Triethanolamine | 0.1000 |
| TOTAL | 100.0000 |

Procedure:

In main kettle, heat Phase I ingredients to 60° C. and mix until uniform. In a separate kettle, premix Phase II ingredients until uniform and add to main kettle. Premix Phase III ingredients until uniform and add into main kettle. Premix Phase IV ingredients until uniform and add into main kettle. Mix batch in main kettle with a homogenizing mixer for 15 minutes while maintaining the temperature at 60° C. Premix Phase V ingredients until clear. Cool the batch in the main kettle to 30° C. Add Phase V ingredients to the batch and mix until uniform. The final pH of the batch is 5.35.

Example 2

Clinical Study

This study was designed to determine the skin lightening efficacy of the 2-pyridylmethylsulfinyl-benzimidazoles.

Ten female volunteers, aged 18-45 and having skin type I-II (Fitzpatrick, T. B., Ultraviolet-induced Pigmentary Changes: benefits and hazards, *Curr. Probl. Dermatol.* 15:25-38, 1986) were recruited from a local population in New York State. Qualified panelists were in normal health with no evidence of acute or chronic disease including dermatologic problems. Subjects exhibiting current sunburn, rashes, scratches, burn marks, etc., which might interfere with the evaluation of test results were excluded from the study. Pregnant or lactating females were also excluded. On examination, the test site of each subject was devoid of excessive warts, nevi, moles, sunburn, suntan, scars and active dermal lesions. The panelists were not using systemic or topical retinoids, antihistamines or similar agents currently, had not been using such products for at least two weeks prior to commencement of the study, and agreed that they will not use such products during the course of the study. The subjects expressed willingness to cooperate with the investigator and demonstrated the ability to understand the purpose of the study and the risks associated with participating in the study. Panelists signed an informed consent form prior to the initiation of the study.

Distinct areas (approximately 4 cm$^2$) corresponding to the test materials were marked on the backs of the panelists. Additional sites were marked as the untreated, unirradiated and the untreated, irradiated sites. The sites were exposed to a single irradiation exposure of 3.5 MEDs of UVB. The source of radiation was a Xenon Arc Solar Simulator (150 Watt) with filters (mm UG-5) to expose the skin to UV-B and UV-A irradiation. Immediately after irradiation, the sites were treated with the test materials every day (with the exception of Saturdays and Sundays) for four weeks. Test material 1 is the formulation in Table II of Example 1. Comparative Test material 1 is provided below in Table III. Chromameter readings (reflectance values) were obtained using a Minolta Chromameter twice a week for four weeks. The Chromameter measures the difference in reflectance, L*, of the skin. The change in the value of the difference in reflectance, ΔL* on each of the days on which measurements are taken is measured against a baseline skin color value of the untreated unirradiated skin measured at every time point. The observed reflectance values for all time points are recorded on a graph, and the area under the curve for each test site is calculated. The skin-lightening factor is calculated as the area under the curve of the treated site subtracted from the area under the curve of the untreated site.

As shown in the FIGURE, the composition containing the omeprazole exhibited an excellent skin-lightening effect at both 3 weeks and 4 weeks of treatment, having respective lightening factors of 3.08 and 4.63. In contrast, the comparative test formulation containing kojic acid (more than 500 times the concentration of the omeprazole) exhibited lightening indices of 2.01 and 3.14 at 3 weeks and 4 weeks, respectively.

The results obtained using the omeprazole-containing formula are particularly impressive in comparison with the results obtained in another study using 4% hydroquinone. The lightening factors observed for the hydroquinone were 3.2 and 5.0, at 3 weeks and 4 weeks of treatment, respectively.

TABLE III

COMPARATIVE SKIN-LIGHTENING COMPOSITION

| MATERIAL | WEIGHT PERCENT |
|---|---|
| Phase I | |
| Water/phenyltrimethicone/cyclomethicone/ dimethiconol/phosphoglycerides/ carbomer/triethanolamine | 50.00 |
| Sodium dehydroacetate | 0.10 |
| Disodium EDTA | 0.14 |
| Phase II | |
| Glycerin | 3.00 |
| Aluminum starch octenylsuccinate | 1.00 |
| Phase III | |
| Purified water | 39.81 |
| Acrylates/C10-30 alkyl acrylate crosspolymer | 0.30 |
| Carbomer | 0.35 |
| Kojic acid | 2.00 |

TABLE III-continued

COMPARATIVE SKIN-LIGHTENING COMPOSITION

| MATERIAL | WEIGHT PERCENT |
|---|---|
| Phase IV | |
| Glycerin | 1.00 |
| Xanthan gum | 0.20 |
| Phase V | |
| Purified water | 1.00 |
| Triethanolamine | 0.20 |
| TOTAL | 100.00 |

Procedure:

In main kettle, heat Phase I ingredients to 60° C. and mix until uniform. In a separate kettle, premix Phase II ingredients until uniform and add to main kettle. Premix Phase III ingredients until uniform and add into main kettle. Premix Phase IV ingredients until uniform and add into main kettle. Mix batch in main kettle with a homogenizing mixer for 15 minutes while maintaining the temperature at 60° C. Premix Phase V ingredients until clear. Cool the batch in the main kettle to 30° C. Add Phase V ingredients to the batch and mix until uniform. The final pH of the batch is 5.12.

That omeprazole can be used in a formulation to lighten the skin is a surprising and unexpected discovery, since one skilled in the art could not have predicted that a stomach acid inhibitor would be at least as effective as a standard lightening agent, kojic acid (which is used at almost 600 times the concentration of omeprazole) and comparable to the use of a formulation containing 4% hydroquinone (which is used at more than 1,000 times the concentration of omeprazole, and above the 2% legal limit for its use in consumer products).

The mechanism of action of the inhibitors of Type I H+, K+-ATPases in skin lightening/depigmentation is under investigation. The inventors have previously determined that, while 250 μg/ml of omeprazole is required to moderately inhibit human tyrosinase activity in test tube assay using extracts from human melanocytes, to inhibit melanogensis in cultured melanocytes, the effective concentration of omeprazole is approximately 5-50 μg/ml. Therefore, the mechanism of inhibition of melanogenesis by omeprazole does not appear to be direct inhibition of tyrosinase activity. Additionally, the inventors have determined, by treating cells with omeprazole, extracting the total RNA and measuring the levels of tyrosinase or MITF specific mRNA using gene-specific complementary primers and RT-PCR, that omeprazole does not change tyrosinase or MITF mRNA levels in B16F10 mouse melanoma cells. Omeprazole decreases tyrosinase protein level, as determined by analysis with Western blots using antibodies specific for mouse tyrosinase. It was also observed, using an assay for tyrosinase with L-DOPA as a substrate, that omeprazole decreases the tyrosinase activity of B16F10 cell extracts. It is possible that the pH of the melanosome, aside from regulating tyrosinase activity, also regulates trafficking and maturation of tyrosinase. Thus, a change in pH may also reduce the amount of tyrosinase protein as well as decreasing its activity.

Ancans et al. (2001), supra, has suggested that, as the p-locus protein (which may be a Na+/H+ antiporter) in melanosomes mediates the neutralization of melanosomal pH, this protein could be a key control point for skin pigmentation. However, this protein too does not appear to be the target for omeprazole. The inventors have demonstrated, by protein sequence comparison with the known target protein of omeprazole in human parietal cells, that the p-locus protein and the gastric pump have no sequence homology, that is, there are no cysteines in the p-locus protein, which are comparable to those in the gastric pump, to bind omeprazole. The inventors have further determined that the only known target for omeprazole binding, the protein ATP4A (gastric pump), does not appear to be expressed in human melanocytes because, as determined using gene-specific primers and RT-PCR, the mRNA for the gastric pump is not found in melanocytes. Thus, surprisingly, the PPI inhibitor compounds may not function in the same way in the melanosome (if the target is in the melanosome) as they do in the parietal cells of the stomach. Studies of proteins ATPA7 and ATP12A, which are also present in gastric parietal cells, and which are structurally related to ATP4A, indicate that each of these pumps do not contain cysteines in a locus appropriate for omeprazole binding. Thus the mechanism of action of omeprazole and other inhibitors of Type I H+, K+-ATPases in inhibiting melanogenesis is novel and unexpected from any of the prior art teachings.

While the subject invention have been described in various preferred embodiments, the skilled artisan will appreciate that various modifications, substitutions, omissions and changes may be made without departing from the spirit thereof.

What is claimed is:

1. A composition for lightening or depigmenting skin, comprising from about 0.00005 weight percent to about 0.5 weight percent of (3-(cyanomethyl)-2-methyl-8-phenyl-methoxy-imidazo[1,2-a]pyridine); and
   a sun protection agent;
   formulated into a topically applicable, cosmetically or dermatologically acceptable vehicle, carrier or diluent therefor wherein the composition for lightening or depigmenting skin is in the form of an emulsion, an anhydrous composition, an aqueous-based solution, a suspension, a dispersion, a lotion, a serum, an essence, a milk, a cream, a gel, a paste, an ointment, a spray, a stick, a mousse, an aerosol or microcapsules.

2. The composition of claim 1, further comprising an additional skin-lightening agent.

3. A method of lightening or depigmenting skin, comprising applying to skin in need of such treatment a composition according to claim 1.

* * * * *